(12) United States Patent
Hayashizaki

(10) Patent No.: US 8,809,518 B2
(45) Date of Patent: Aug. 19, 2014

(54) OLIGONUCLEOTIDE LINKERS COMPRISING A VARIABLE COHESIVE PORTION AND METHOD FOR THE PREPARATION OF POLYNUCLEOTIDE LIBRARIES BY USING SAID LINKERS

(75) Inventor: Yoshihide Hayashizaki, Tsukuba (JP)

(73) Assignee: Riken, Saitama (JP)

(*) Notice: Subject to any disclaimer, the term of this patent is extended or adjusted under 35 U.S.C. 154(b) by 152 days.

(21) Appl. No.: 12/897,745

(22) Filed: Oct. 4, 2010

(65) Prior Publication Data

US 2012/0028313 A1 Feb. 2, 2012

Related U.S. Application Data

(62) Division of application No. 11/773,948, filed on Jul. 5, 2007, now abandoned, which is a division of application No. 10/398,483, filed as application No. PCT/JP01/08805 on Oct. 5, 2001, now abandoned.

(30) Foreign Application Priority Data

Oct. 5, 2000 (JP) .................................. 2000-306749

(51) Int. Cl.
*C07H 21/00* (2006.01)
*C12Q 1/68* (2006.01)
*C12P 19/34* (2006.01)

(52) U.S. Cl.
USPC .......... 536/25.3; 435/6.1; 435/6.12; 435/91.2

(58) Field of Classification Search
USPC ......................... 435/6.1, 6.12, 91.2; 536/25.3
See application file for complete search history.

(56) References Cited

U.S. PATENT DOCUMENTS

| 4,661,450 A * | 4/1987 | Kempe et al. .............. 435/91.41 |
| 7,482,443 B2 | 1/2009 | Shafer |

FOREIGN PATENT DOCUMENTS

| EP | 0622457 A1 | 11/1994 |
| EP | 0625572 A1 | 11/1994 |
| EP | 0645449 A1 | 3/1995 |
| EP | 0990702 A1 | 4/2000 |
| EP | 01016729 A1 | 7/2000 |
| JP | 07-177885 A | 7/1995 |
| JP | 2007-177885 A | 7/2007 |
| WO | WO-93/18178 A1 | 9/1993 |
| WO | WO-95/13369 A1 | 5/1995 |
| WO | WO-98/02449 A1 | 1/1998 |
| WO | WO-98/15652 A1 | 4/1998 |
| WO | WO-98/51789 A2 | 11/1998 |
| WO | WO-98/56943 A1 | 12/1998 |
| WO | WO-00/56878 A1 | 9/2000 |
| WO | WO-00/56913 A1 | 9/2000 |
| WO | WO-01/66802 A1 | 9/2001 |

OTHER PUBLICATIONS

Carninci, P. et al. "High-Efficiency Full-Length cDNA Cloning," Methods in Enzymology, vol. 303, pp. 19-44 (1999).
Sambrook, K. et al., Molecular cloning: a laboratory manual, 2nd ed., pp. 5.61-5.67 (1989).
Shibata Y. et al., "Cloning Full-length, Cap-Trapper-selected cDNAs by using the single-strand linker ligation method.", Biotechniques, vol. 30, No. 6, Jun. 2001, pp. 1250-1254.
Suzuki, Y. et al., "Construction and characterization of a full length-enriched and a 5@?-end-enriched cDNA library", Gene: An International Journal on Genes and Genomes, Elsevier Science Publishers, Barking, GB, vol. 200, No. 1-2, Oct. 24, 1997, pp. 149-156.
Maruyama, K. et al., "Oligo-capping: A simple method to replace the cap structure of eurokaryotic mRNAs with oligonucleotides", Gene, Elsevier Biomedical Press, Amsterdam, NL, vol. 138, 1994, pp. 171-174.
Liu, Xiuwen at al., "Mapping and 5' and 3' ends of *Tetrahymena thermophila* mRNAs using RNA ligase mediated amplification of cDNA ends (RLM-RACE)", Nucleic Acids Research, Oxford University Press, Surrey, GB, vol. 21, No. 21, 1993, pp. 4954-4960.
Edery, I. et al., "An effecient strategy to isolate full-length cDNAs based on an mRNA cap retention procedure (capture)", Molecular and Cellular Biology, Washington, DC, US, vol. 15, Jun. 1995, pp. 3363-3371.
Japanese Office Action 2002-532458, Jun. 13, 2008.
Guilfoyle, Richard A. et al., "Ligation-mediated PCR amptication of specific fragments from a Class-II restriction endonuclease total digest", Nucleic Acids Research, 1997, vol. 25, No. 9, pp. 1869-01873.
Unrau, Paul et al., "Non-cloning amplification of specific DNA fragments from whole genomic DNA digests using DNA 'indexers'", Gene, vol. 145, 1994, pp. 163-169.
International Search Report issued in International Application No. PCT/JP2001/08805.

* cited by examiner

*Primary Examiner* — Ardin Marschel
(74) *Attorney, Agent, or Firm* — Birch, Stewart, Kolasch & Birch, LLP

(57) ABSTRACT

The present invention relates to a linker or population of linkers that include an oligonucleotide fixed portion and an oligonucleotide variable portion represented by formula (N)n, wherein N is A, C, G, T or U, or their derivatives, and n is an integer equal to or higher than 1. A linker-polynucleotide or a population of linker-polynucleotides of the invention may be constituted by said linker or population of linkers and a target first strand polynucleotide bound to said linker. The invention also encompasses a method of preparing said linker or population of linkers and a method of preparing a linker-polynucleotide using said linker or population of linkers. The linkers or polynucleotide-linkers of the invention can be used in a method of preparing a cDNA library.

26 Claims, 20 Drawing Sheets

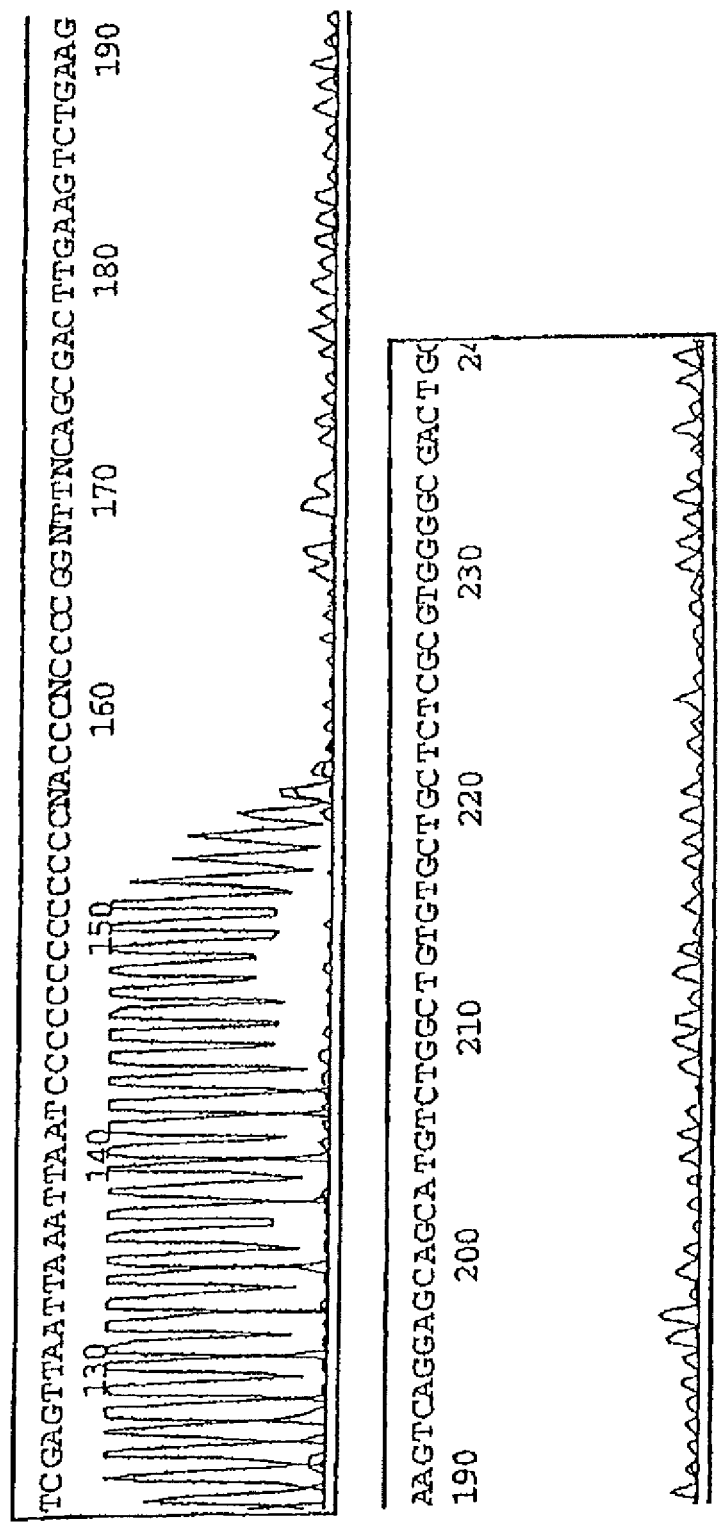

Fig.5(c)

CGGCGGGCGGTTGCGGGCGCGAGCTTCCCGGGTGCTGAGGGAATTCACGGNGAGGCGCCGCCCGC
240    250        260        270        280        290        300

CCGCTGCACACCAGCCTGCAGAGCTGNTCGTTCGCCAAGGAGCTNTTTCTGGGCAAC
300    310        320        330        340        350

SEQUENCE LISTING

```
<160> NUMBER OF SEQ ID NOS: 32

<210> SEQ ID NO 1
<211> LENGTH: 49
<212> TYPE: DNA
<213> ORGANISM: Artificial Sequence
<220> FEATURE:
<223> OTHER INFORMATION: Description of Artificial Sequence: GN5 linker
      upper strand
<220> FEATURE:
<221> NAME/KEY: misc_feature
<222> LOCATION: (45)..(49)
<223> OTHER INFORMATION: n = any nucleotide

<400> SEQUENCE: 1
agagagagag ctcgagctct atttaggtga cactatagaa ccagnnnnn          49

<210> SEQ ID NO 2
<211> LENGTH: 43
<212> TYPE: DNA
<213> ORGANISM: Artificial Sequence
<220> FEATURE:
<223> OTHER INFORMATION: Description of Artificial Sequence: linker
      lower strand

<400> SEQUENCE: 2
tggttctata gtgtcaccta aatagagctc gagctctctc tct                43
```

```
<210> SEQ ID NO 3
<211> LENGTH: 49
<212> TYPE: DNA
<213> ORGANISM: Artificial Sequence
<220> FEATURE:
<223> OTHER INFORMATION: Description of Artificial Sequence: N6 linker
      upper strand
<220> FEATURE:
<221> NAME/KEY: misc_feature
<222> LOCATION: (44)..(49)
<223> OTHER INFORMATION: n = any nucleotide

<400> SEQUENCE: 3
agagagagag ctcgagctct atttaggtga cactatagaa ccannnnnn                49

<210> SEQ ID NO 4
<211> LENGTH: 43
<212> TYPE: DNA
<213> ORGANISM: Artificial Sequence
<220> FEATURE:
<223> OTHER INFORMATION: Description of Artificial Sequence: primer
      comprising BamHI site
<220> FEATURE:
<221> NAME/KEY: misc_feature
<222> LOCATION: (42)..(42)
<223> OTHER INFORMATION: v = g or c or a
<220> FEATURE:
<221> NAME/KEY: misc_feature
<222> LOCATION: (43)..(43)
<223> OTHER INFORMATION: n = any nucleotide

<400> SEQUENCE: 4
gagagagaga aggatccaag agctcttttt ttttttttt tvn                       43

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: M13 forward
      primer

<400> SEQUENCE: 5
tgtaaaacga cggccagt                                                  18

<210> SEQ ID NO 6
<211> LENGTH: 106
<212> TYPE: DNA
<213> ORGANISM: Artificial Sequence
<220> FEATURE:
<223> OTHER INFORMATION: Description of Artificial Sequence: Upper
      strand of Not/Kpn double strand oligonucleotide

<400> SEQUENCE: 6
ggccgcataa cttcgtatag catacattat acgaagttat ggatcaggcc aaatcggccg    60
agctcgaatt cgtcgacgag agactgcagg agagaggatc cggtac                  106

<210> SEQ ID NO 7
<211> LENGTH: 98
<212> TYPE: DNA
<213> ORGANISM: Artificial Sequence
<220> FEATURE:
<223> OTHER INFORMATION: Description of Artificial Sequence: Lower
      strand of Not/Kpn double strand oligonucleotide

<400> SEQUENCE: 7
cggatcctct ctcctgcagt ctctcgtcga cgaattcgag ctcggccgat ttggcctgat    60
ccataacttc gtataatgta tgctatacga agttatgc                           98
```

```
<210> SEQ ID NO 8
<211> LENGTH: 40
<212> TYPE: DNA
<213> ORGANISM: Artificial Sequence
<220> FEATURE:
<223> OTHER INFORMATION: Sequence used in the preparation of a
      full-length cDNA library

<400> SEQUENCE: 8
aaaaaaaaaa aaaaaaaaaa aaaaaaaaaa aaaaaaaaaa                            40

<210> SEQ ID NO 9
<211> LENGTH: 35
<212> TYPE: DNA
<213> ORGANISM: Artificial Sequence
<220> FEATURE:
<223> OTHER INFORMATION: Sequence used in the preparation of a
      full-length cDNA library
<220> FEATURE:
<221> NAME/KEY: misc_feature
<222> LOCATION: (35)..(35)
<223> OTHER INFORMATION: n is a, c, g, or t

<400> SEQUENCE: 9
gaaggatcca agagctcttt tttttttttt tttvn                                 35

<210> SEQ ID NO 10
<211> LENGTH: 16
<212> TYPE: DNA
<213> ORGANISM: Artificial Sequence
<220> FEATURE:
<223> OTHER INFORMATION: Sequence used in the preparation of a
      full-length cDNA library

<400> SEQUENCE: 10
aaaaaaaaaa aaaaaa                                                      16

<210> SEQ ID NO 11
<211> LENGTH: 49
<212> TYPE: DNA
<213> ORGANISM: Artificial Sequence
<220> FEATURE:
<223> OTHER INFORMATION: Sequence used in the preparation of a
      full-length cDNA library
<220> FEATURE:
<221> NAME/KEY: misc_feature
<222> LOCATION: (45)..(49)
<223> OTHER INFORMATION: n is a, c, g, or t

<400> SEQUENCE: 11
agagagagag ctcgagctct atttaggtga cactatagaa ccagnnnnn                  49

<210> SEQ ID NO 12
<211> LENGTH: 43
<212> TYPE: DNA
<213> ORGANISM: Artificial Sequence
<220> FEATURE:
<223> OTHER INFORMATION: Sequence used in the preparation of a
      full-length cDNA library

<400> SEQUENCE: 12
tggttctata gtgtcaccta aatagagctc gagtctctct ctc                        43

<210> SEQ ID NO 13
<211> LENGTH: 33
<212> TYPE: DNA
<213> ORGANISM: Artificial Sequence
```

```
<220> FEATURE:
<223> OTHER INFORMATION: Sequence used in the preparation of a
      full-length cDNA library

<400> SEQUENCE: 13
aaaaaaaaaa aaaaaagagc tcttggatcc tga                                   33

<210> SEQ ID NO 14
<211> LENGTH: 38
<212> TYPE: DNA
<213> ORGANISM: Artificial Sequence
<220> FEATURE:
<223> OTHER INFORMATION: Sequence used in the preparation of a
      full-length cDNA library
<220> FEATURE:
<221> NAME/KEY: misc_feature
<222> LOCATION: (34)..(38)
<223> OTHER INFORMATION: n is a, c, g, or t

<400> SEQUENCE: 14
tcgagctcta tttaggtgac actatagaac cagnnnnn                              38

<210> SEQ ID NO 15
<211> LENGTH: 29
<212> TYPE: DNA
<213> ORGANISM: Artificial Sequence
<220> FEATURE:
<223> OTHER INFORMATION: Sequence used in the preparation of a full
      length cDNA library

<400> SEQUENCE: 15
ctggttctat agtgtcacct aaatagagc                                        29

<210> SEQ ID NO 16
<211> LENGTH: 25
<212> TYPE: DNA
<213> ORGANISM: Artificial Sequence
<220> FEATURE:
<223> OTHER INFORMATION: Sequence used in the preparation of a
      full-length cDNA library

<400> SEQUENCE: 16
aaaaaaaaaa aaaaaagagc tcttg                                            25

<210> SEQ ID NO 17
<211> LENGTH: 29
<212> TYPE: DNA
<213> ORGANISM: Artificial Sequence
<220> FEATURE:
<223> OTHER INFORMATION: Sequence used in the preparation of a
      full-length cDNA library

<400> SEQUENCE: 17
gatccaagag ctcttttttt tttttttt                                         29

<210> SEQ ID NO 18
<211> LENGTH: 126
<212> TYPE: DNA
<213> ORGANISM: Artificial Sequence
<220> FEATURE:
<223> OTHER INFORMATION: Sequence illustrated in Figure 5 of a
      sequencing chart of a cDNA sequence having G-tail described in the
      prior art
```

-continued

<400> SEQUENCE: 18
gaattgtaat acgactcact atagggcgaa ttggagctcc accgcgggtg gcggccgcat     60
aacttcgtat atagcataca ttatacgaag ttatggatca ggccaaatcg gccgagctcg    120
aattcg                                                               126

<210> SEQ ID NO 19
<211> LENGTH: 119
<212> TYPE: DNA
<213> ORGANISM: Artificial Sequence
<220> FEATURE:
<223> OTHER INFORMATION: Sequence illustrated in Figure 5 of a
      sequencing chart of a cDNA sequence having G-tail described in the
      prior art
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t

<400> SEQUENCE: 19
tcgagttaat taaattaatc cccccccccc ccnacccncc ccggnttnca gcgacttgaa     60
gtctgaagaa gtcaggagca gcatgtctgg ctgtgtgctg ctctcgcgtg gggcgactg    119

<210> SEQ ID NO 20
<211> LENGTH: 119
<212> TYPE: DNA
<213> ORGANISM: Artificial Sequence
<220> FEATURE:
<223> OTHER INFORMATION: Sequence illustrated in Figure 5 of a
      sequencing chart of a cDNA sequence having G-tail described in the
      prior art
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t

<400> SEQUENCE: 20
ggcggcggtt gcggcgcgag cttcccgggt gctgagggaa ttcacggnga ggcgccgccc     60
gcccgctgca caccagcctg cagagctgnt cgttcgccaa ggagctnttt ctgggcaac    119

<210> SEQ ID NO 21
<211> LENGTH: 117
<212> TYPE: DNA
<213> ORGANISM: Artificial Sequence
<220> FEATURE:
<223> OTHER INFORMATION: Sequence illustrated in Figure 5 of a
      sequencing chart of a cDNA sequence having G-tail described in the
      prior art <220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t

<400> SEQUENCE: 21
atngnncaga aggagttttt cccatttnca gaggtcnttc ancatgaact tanngaanng    60
aaatcaantc anttcgtggg accgntggaa aaattnttca ctgaaaaant ggactct    117

<210> SEQ ID NO 22
<211> LENGTH: 112
<212> TYPE: DNA
<213> ORGANISM: Artificial Sequence
<220> FEATURE:
<223> OTHER INFORMATION: Sequence illustrated in Figure 5 of a
      sequencing chart of a cDNA sequence having G-tail described in the
      prior art
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t

```
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (77)..(78)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t

<400> SEQUENCE: 22
ngaaaaattg accatnnagg gaaaattcat tttgacacct tnaaaaantt tgaagaaaaa    60
gcctgtgact tttttgnntt acnangtccc anaaanaata tngttggnct gn           112

<210> SEQ ID NO 23
<211> LENGTH: 117
<212> TYPE: DNA
<213> ORGANISM: Artificial Sequence
<220> FEATURE:
<223> OTHER INFORMATION: Sequence illustrated in Figure 6 showing a
      sequencing chart of a cDNA sequence ligated with N6/GN6 linker
      mixture.

<400> SEQUENCE: 23
gaattgttat accgactcac tatagggcga attggagctc caccgcggtg gcggccgcat    60
aataacttcg tatagcatac attatacgaa gttatggatc aggccaaatc ggccgag      117

<210> SEQ ID NO 24
<211> LENGTH: 108
<212> TYPE: DNA
<213> ORGANISM: Artificial Sequence
<220> FEATURE:
<223> OTHER INFORMATION: Sequence illustrated in Figure 6 showing a
      sequencing chart of a cDNA sequence ligated with N6/GN6 linker
      mixture.

<400> SEQUENCE: 24
ctcgaattcg tcgagctcta tttaggtgac actatagaac cagaggctga gccggctgct    60
atttgaaggg agcgcgctga gcggaggagc gcttcagagg gaagagtt                108
```

```
<210> SEQ ID NO 25
<211> LENGTH: 103
<212> TYPE: DNA
<213> ORGANISM: Artificial Sequence
<220> FEATURE:
<223> OTHER INFORMATION: Sequence illustrated in Figure 6 showing a
      sequencing chart of a cDNA sequence ligated with N6/GN6 linker
      mixture.

<400> SEQUENCE: 25
gggagacgca gggaggtttc cgtcctgtcg tccccccctt cttctctgtc gccgcaagtc      60
actgtgaaga agtctccaca gcagctgcgg ctcccgggcg cgg                      103

<210> SEQ ID NO 26
<211> LENGTH: 102
<212> TYPE: DNA
<213> ORGANISM: Artificial Sequence
<220> FEATURE:
<223> OTHER INFORMATION: Sequence illustrated in Figure 6 showing a
      sequencing chart of a cDNA sequence ligated with N6/GN6 linker
      mixture.

<400> SEQUENCE: 26
gatggccaag gtgtcggtgc tgaatgtggc tgtgctggag aacccgagcc cccctttcca      60
cagccccttc cggttcgaga tcagcttcga atgcagtgag gc                       102

<210> SEQ ID NO 27
<211> LENGTH: 102
<212> TYPE: DNA
<213> ORGANISM: Artificial Sequence
<220> FEATURE:
<223> OTHER INFORMATION: Sequence illustrated in Figure 6 showing a
      sequencing chart of a cDNA sequence ligated with N6/GN6 linker
      mixture.

<400> SEQUENCE: 27
cctgtctgac gacctggagt ggaagatcat ttatgtgggc tcagctgaga gtagtgagga      60
gtttgatcag atcctagatt cagtgctggt gggccctgtc cc                       102

<210> SEQ ID NO 28
<211> LENGTH: 114
<212> TYPE: DNA
<213> ORGANISM: Artificial Sequence
<220> FEATURE:
<223> OTHER INFORMATION: Sequence illustrated in Figure 7 showing a
      sequencing chart of a cDNA sequence ligated with GN5 linker.

<400> SEQUENCE: 28
gattgaatac gactcactat agggcgaatt ggagctccac cgcggtggcg gccgcataac      60
tacttcgtat agcatacatt atacgaagtt atggatcagg ccaaatcggc cgag          114

<210> SEQ ID NO 29
<211> LENGTH: 107
<212> TYPE: DNA
<213> ORGANISM: Artificial Sequence
<220> FEATURE:
<223> OTHER INFORMATION: Sequence illustrated in Figure 7 showing a
      sequencing chart of a cDNA sequence ligated with GN5 linker.

<400> SEQUENCE: 29
ctcgaattcg tcgagctcta tttaggtgac actatagaac caggcgaacg gcgagcagcg      60
gcggcggcgg cgcggaagt gcagcggagg tttttgctgg tttcgga                  107
```

```
<210> SEQ ID NO 30
<211> LENGTH: 103
<212> TYPE: DNA
<213> ORGANISM: Artificial Sequence
<220> FEATURE:
<223> OTHER INFORMATION: Sequence illustrated in Figure 7 showing a
      sequencing chart of a cDNA sequence ligated with GN5 linker.

<400> SEQUENCE: 30
cccagcggcc ggatggtgaa atcctccctg cagcggatcc tcaacagcca ctgctgcttc      60
gccagagaga aggaagggga caaacgcagc gccacgcttc acg                       103

<210> SEQ ID NO 31
<211> LENGTH: 101
<212> TYPE: DNA
<213> ORGANISM: Artificial Sequence
<220> FEATURE:
<223> OTHER INFORMATION: Sequence illustrated in Figure 7 showing a
      sequencing chart of a cDNA sequence ligated with GN5 linker.

<400> SEQUENCE: 31
cagccgcacc atgccgcttc ttagtcagca cagccgcggc ggctgcagca gcgacgagag      60
ttctagggtt gcccttaatt gctgtagtaa cctgggtccg g                        101

<210> SEQ ID NO 32
<211> LENGTH: 104
<212> TYPE: DNA
<213> ORGANISM: Artificial Sequence
<220> FEATURE:
<223> OTHER INFORMATION: Sequence illustrated in Figure 7 showing a
      sequencing chart of a cDNA sequence ligated with GN5 linker.

<400> SEQUENCE: 32
ggcctcggtg gtgctcctga tgtccctcac ccaccctga agatcccagg tgggcgagcg       60
agggaacagt cagcgggatc acagtctttc agctagcatc atgt                     104
```

OLIGONUCLEOTIDE LINKERS COMPRISING A VARIABLE COHESIVE PORTION AND METHOD FOR THE PREPARATION OF POLYNUCLEOTIDE LIBRARIES BY USING SAID LINKERS

CROSS-REFERENCE TO RELATED APPLICATIONS

This application is a divisional of U.S. patent application Ser. No. 11/773,948, filed Jul. 5, 2007, which is a divisional of U.S. patent application Ser. No. 10/398,483, filed Apr. 4, 2003, which is the U.S. National Stage of International Application No. PCT/JP01/08805 filed Oct. 5, 2001, which claims priority to Japanese Patent Application No. 2000-306749 filed Oct. 5, 2000, all of which are incorporated herein by reference in their entirety.

TECHNICAL FIELD

The present invention relates to a population of linkers comprising an oligonucleotide fixed portion and an oligonucleotide variable portion and to a method for the preparation of polynucleotide libraries using such population of linkers. Further, the invention relates to an improved linker as a marker for specific libraries.

BACKGROUND ART

Oligonucleotide linkers and primers have been used in the prior art for priming, binding or annealing single strand polynucleotides and allowing the synthesis of the second polynucleotide complementary strand.

All of Carninci et al., 1996, Genomics, 37, 327-336; Carninci et al., 1997, DNA Research 4:61-66; Carninci et al., 1998, Proc. Natl. Acad. Sci USA, 95:520-4; Carninci and Hayashizaki, 1999, Methods Enzymol. 303:19-44, disclose methods for the preparation of cDNA libraries. According to these protocols, a mRNA/cDNA hybrid is prepared and full-coding/full-length cDNAs are selected by mean of the Cap trapper technology, then each single strand cDNA is ligated with a G-tail and the cDNA second strand is synthesized.

However, the G-tailing methodology shows several drawbacks, for example, in sequencing efficiency and translation efficiency when cDNAs clones are used for protein expression.

G-tailing is performed by terminal addition of dGTP using terminal deoxynucleotidyl transferase. However, the number of G residues added is difficult to control and it is variable, generally between 10 and 30. A long G-tail has the drawback of impairing a long read sequencing and lowering the sequencing efficiency, whilst a short G-tail has the drawback of providing a low efficient priming, with the consequence of loss of sample, and necessity of repreparing it.

During a sequencing reaction, long G-stretches (long G-tail) interact with surrounding sequences and form very strong secondary structures. This may be problematic in case of interactions with 5' UTRs that are typically GC rich. In fact, a typical cDNA has 60% GC content in the 5'-UTR that is considered to act as a regulatory region. Similar problems were also observed in cloning vectors having GC rich regions containing a Sfi I or Not I restriction site next to the cloning site.

Further, terminal deoxynucleotidyl transferase used for tailing reaction requires heavy metals, for example, MnCl$_2$ or CoCl$_2$. However, these heavy metals have sometimes caused degradation of cDNAs and decreased rate of production of long strand, full-coding/full-length cDNA.

The purpose of the present invention is to solve these several problems in the prior art and provide a novel and efficient method for the preparation of cDNA libraries.

More specifically, the purpose of the present invention is to provide a novel linker, which can be utilized instead of G-tailing in a method for the preparation of cDNA libraries and to provide a method for the preparation of cDNA libraries using said linker.

DESCRIPTION OF INVENTION

The present invention solves the above-mentioned problems by providing a linker comprising an oligonucleotide fixed portion and an oligonucleotide variable portion, the variable portion being represented as Formula (N)n wherein N is A, C, G, T or U, or their derivatives, and n is an integer equal to or higher than 1. When n is an integer equal to or higher than 2, the nucleotides (N) of the variable portion may be the same or different.

The variable portion is preferably prepared at random.

The linker according to the invention may be a single or a double strand linker.

The present invention further relates to a population of linkers comprising the two or more of the linkers of the present invention.

According to an embodiment of the present invention, a linker or population of linkers is provided that is prepared by;

(a) synthesizing a first oligonucleotide single strand comprising an oligonucleotide single strand fixed portion and an oligonucleotide single strand variable portion, (b) synthesizing a second oligonucleotide single strand comprising an oligonucleotide single strand fixed portion complementary to the first oligonucleotide single strand fixed portion (a), and (c) annealing the first oligonucleotide strand (a) to the second oligonucleotide strand (b) so that the variable portion protrudes outside the double strand fixed linker portion.

The present invention further relates to a linker-polynucleotide product or a population of linker-polynucleotide products comprising the linker or population of linkers according to the present invention and the target first strand polynucleotide bound to the linker.

The present invention still further relates to a vector comprising the linker-polynucleotide according to the present invention.

In addition, the present invention relates to a method for preparing the linker or population of linkers according to the present invention, which comprises the steps of:

(a) synthesizing a first oligonucleotide single strand comprising an oligonucleotide single strand fixed portion and an oligonucleotide single strand variable portion, (b) synthesizing a second oligonucleotide single strand comprising an oligonucleotide single strand fixed portion complementary to the first oligonucleotide single strand fixed portion (a), and, (c) annealing the first oligonucleotide strand (a) to the second oligonucleotide strand (b), so that the variable portion protrudes outside the double strand fixed portion.

The present invention is further directed to the following methods:

(1) a method of binding a target single strand polynucleotide to a linker comprising:

i) the preparation of the linker according to the present invention; and ii) the step of annealing the variable portion of said linker to the target single strand polynucleotide;

(2) a method of binding a target single strand polynucleotide to a linker comprising:
i) the preparation of the linker according to the present invention; and
ii) the step of annealing the variable portion of one (first) strand of said linker to the target single strand polynucleotide and ligating the fixed portion of the other (second) strand of said linker to the target single strand polynucleotide;

(3) a method of binding a target single strand polynucleotide or a population of the polynucleotides to a population of linkers comprising:
i) the preparation of the population of the linker according to the present invention; and
ii) the step of annealing the variable portion of said population of linkers to a population of the target single strand polynucleotides;

(4) a method of binding a target single strand polynucleotide or a population of the target single strand polynucleotides to a population of linkers comprising:
i) the preparation of the population of linkers according to the present invention; and
ii) the step of annealing the variable portion of the first strand of said population of the linkers to the target single strand polynucleotide or the population of the polynucleotides and ligating the fixed portion of the second strand of the population of the linker to the target single strand polynucleotide or the population of the polynucleotides;

(5) a method of preparing a linker-polynucleotide product comprising a linker and a double strand polynucleotide, comprising the steps of:
i) annealing the variable portion of the linker according to the present invention to the target first strand polynucleotide, and
ii) synthesizing the second strand polynucleotide complementary to the target single strand polynucleotide;

(6) a method of preparing a linker-polynucleotide product comprising a linker and a double strand polynucleotide, comprising the steps of:
i) annealing the variable portion of the first strand of the linker according to the present invention to a target single strand polynucleotide and ligating the target single strand polynucleotide to the fixed portion of the second strand of the linker, and
ii) synthesizing the second single strand polynucleotide complementary to said target single strand polynucleotide;

(7) a method of preparing a linker-polynucleotide product comprising a linker or a population of linkers and a population of double strand polynucleotides, comprising the steps of:
i) annealing the variable portion of the linker or a population of the linkers according to the present invention to a target single strand polynucleotide or a population of the target single strand polynucleotides, and
ii) synthesizing the second strand polynucleotide complementary to said target single strand polynucleotide or a population thereof;

(8) a method of preparing a linker-polynucleotide product comprising a linker or a population of linkers and a population of double strand polynucleotides, comprising the steps of:
i) annealing the variable portion of the first strand of the linker or a population of the linkers according to the present invention to a target single strand polynucleotide or a population of the target single strand polynucleotides, ii) ligating the target single strand polynucleotide or the population of the target single strand polynucleotides to the fixed portion of the second strand of the linker or the population of the linkers, and
iii) synthesizing the second single strand polynucleotide(s) complementary to said target single strand polynucleotide(s);

(9) a method of marking a polynucleotide library and distinguishing said library, which comprises the steps of providing a population of linkers comprising a fixed portion and a variable portion (wherein the fixed portion comprises at least one marker indicating the defined tissue or species), and selecting and separating said library by said defined marker;

(10) a method of binding a linker or population of linkers to mRNA, which comprises the steps of:
(a) treating mRNA with a phosphatase and removing phosphate groups from uncapped mRNA,
(b) treating a product of step (a) with a pyrophosphatase, which removes the CAP structure from capped mRNA, and
(c) adding an RNA ligase in the presence of the linker according to the present invention;

(11) a method of preparing a linker-polynucleotide product, which comprises the steps of:
(a) treating mRNA with a phosphatase and removing phosphate groups from uncapped mRNA,
(b) treating a product of step (a) with a pyrophosphatase, which removes the CAP structure from capped mRNA,
(c) adding an RNA ligase in the presence of the linker according to the present invention, and
(d) adding oligo dT and synthesizing a polynucleotide complementary to the complete sequence of said mRNA;

(12) a method of binding a linker and population of linkers according to the present invention to a target single strand polynucleotide or population of polynucleotides comprising adding RNA ligase to a mixture of such linker(s) and polynucleotide(s);

(13) a method of preparing DNA/RNA hybrids, which comprises the steps of:
i) providing a full-length/coding or long poly-A mRNAs,
ii) ligating and annealing said mRNAs to the linker of the present invention, the linker comprising a first restriction enzyme site,
iii) annealing oligo dT-primers comprising a second restriction enzyme site to the mRNA,
iv) synthesizing cDNA strands,
v) isolating the hybrids by using restriction enzymes which recognize the two specific restriction enzyme sites introduced, and
vi) cloning;

(14) a method of preparing a linker-polynucleotide product comprising a linker and a single strand polynucleotide, comprising annealing the variable portion of the linker according to the present invention to the target first strand polynucleotide.

PolyA+RNA is transcribed (A) and subsequently oxidized and attached to biotin. After RNase I treatment (B), only full-length cDNA has biotin and trapped with avidin coated magnetic beads (C).

Figure 1:
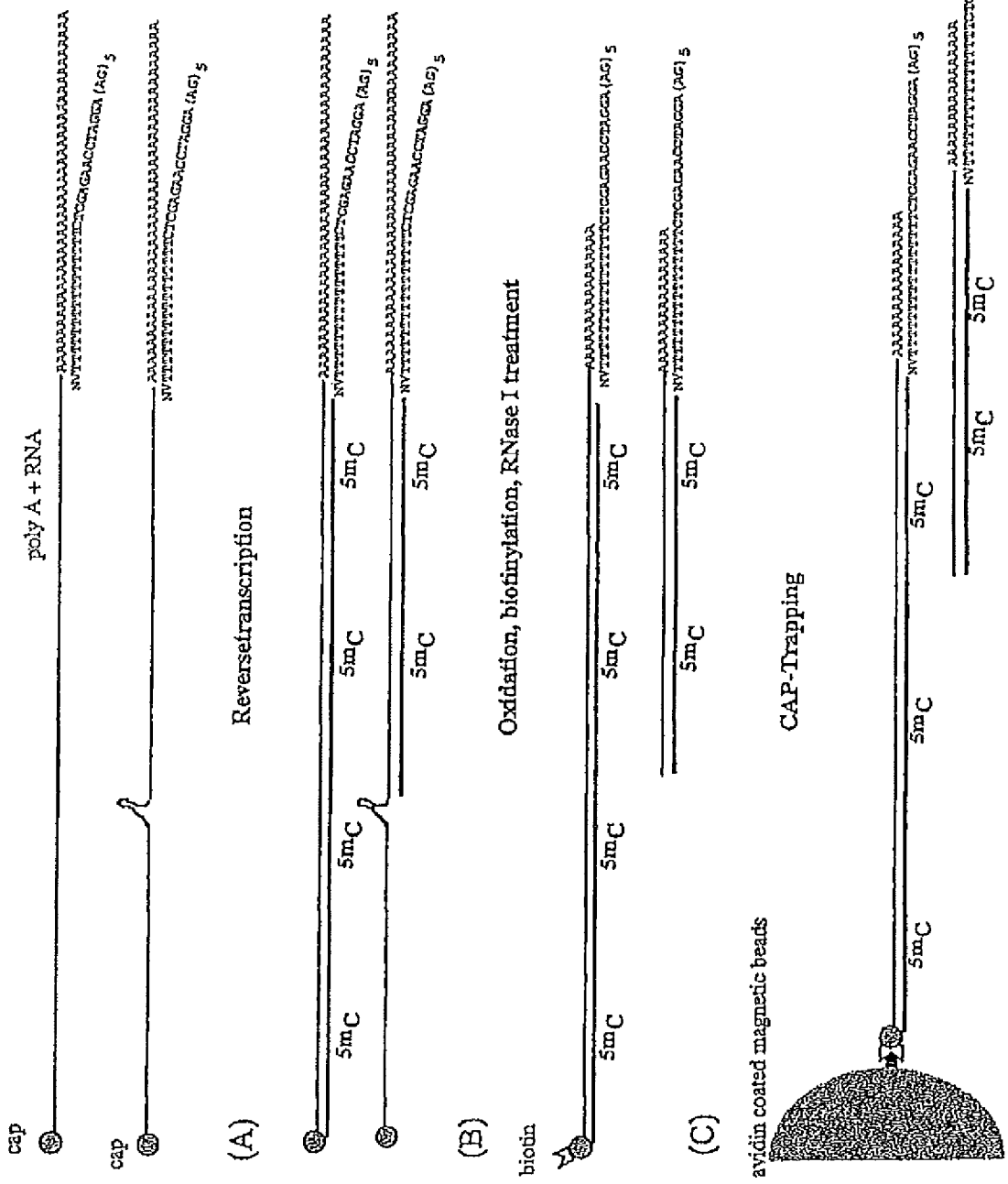
FIG. 1 (SEQ ID NOS: 1-3) shows an example of the procedure for preparation of full-length cDNA library using, as an example, a population of linkers comprising the variable portion GNNNNN.
Figure 2:
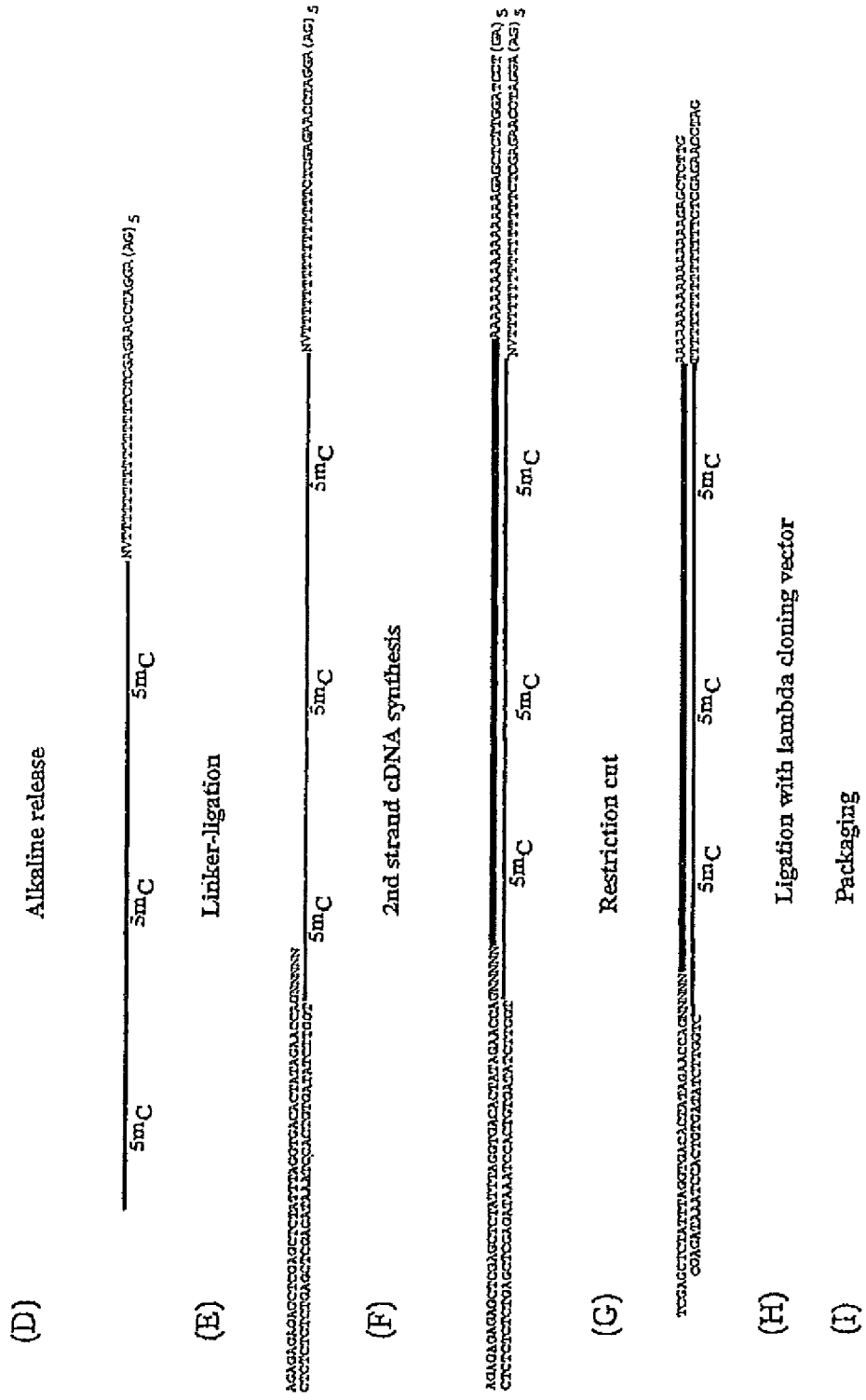

FIG. 2 (SEQ ID NOS: 9, 11-17) shows an example of the procedure for preparation of full-length cDNA library using, as an example, a population of linkers comprising the variable portion GNNNNN, as a continuation of FIG. 1.

The cDNA is released from beads by alkaline treatment and recovered (D), and the linker is ligated (E). A $GN_5$ linker is shown. In the case of a N6 linker, the variable portion is NNNNNN instead of GNNNNN. The second strand cDNA is synthesized (F) and digested with a restriction enzyme (G) and ligated into lambda phage vector (H) as well as packaged (I).

Figure 3:
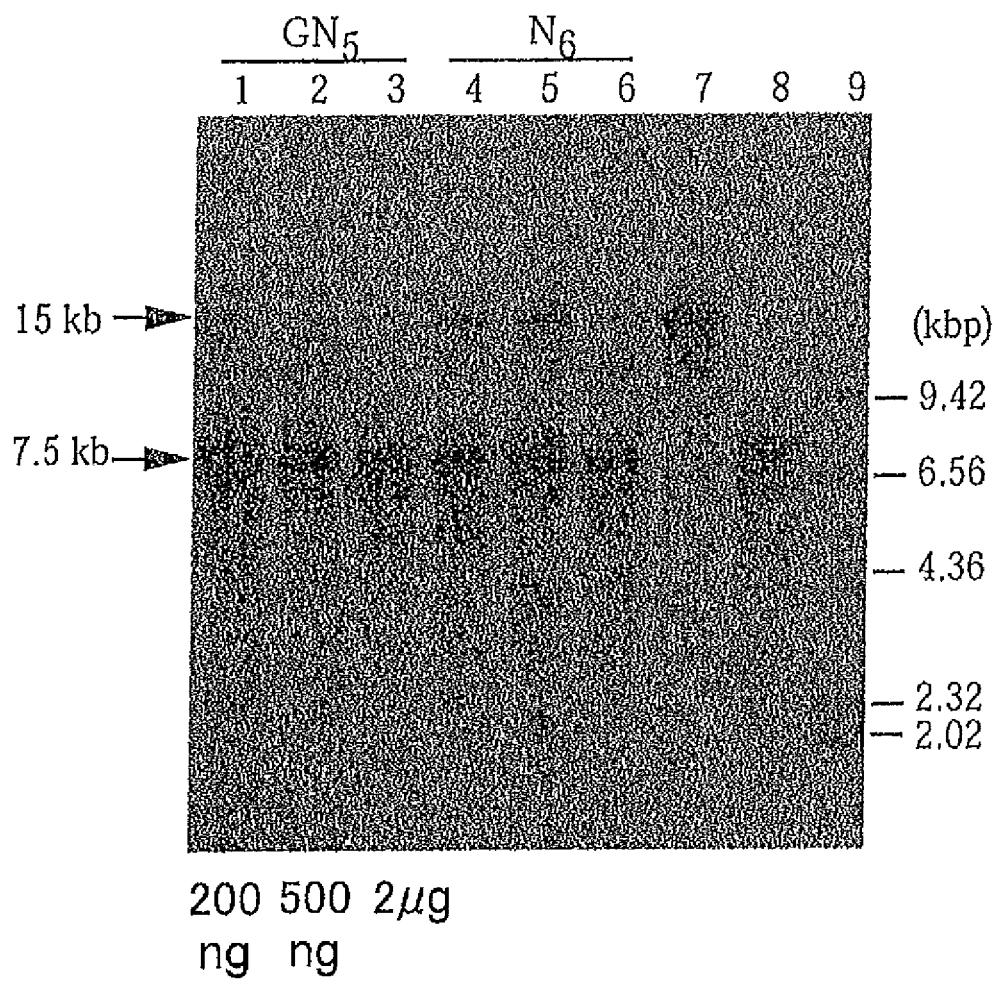

FIG. 3 shows the result of the ligation between the tested cDNA and the linker.

The tested first strand cDNA prepared from 5 µg of 7.5 kb poly(A)-tailed RNA (LifeTechnologies) was used as a starting material. The linker ($GN_5$—, Lanes 1 to 3; $N_6$, Lanes 4 to 6) was annealed to ligate with 50 ng of 7.5 kb tested cDNA. Subsequently, 10 ng sample of linker-binding material was used for synthesizing the second strand cDNA, and then subjected to 0.8% alkali gel electrophoresis.

Linkers were used in different amounts: 200 ng for Lanes 1 and 4; 500 ng for Lanes 2 and 5, and 2 µg for Lanes 3 and 6). As a control, cDNA without linkers was used as a template of the second strand synthesis (Lane 7). Lane 8 is a sample of the first strand cDNA without linkers. Lane 9 is a sample of λ/HindDIII size marker.

Figure 4:
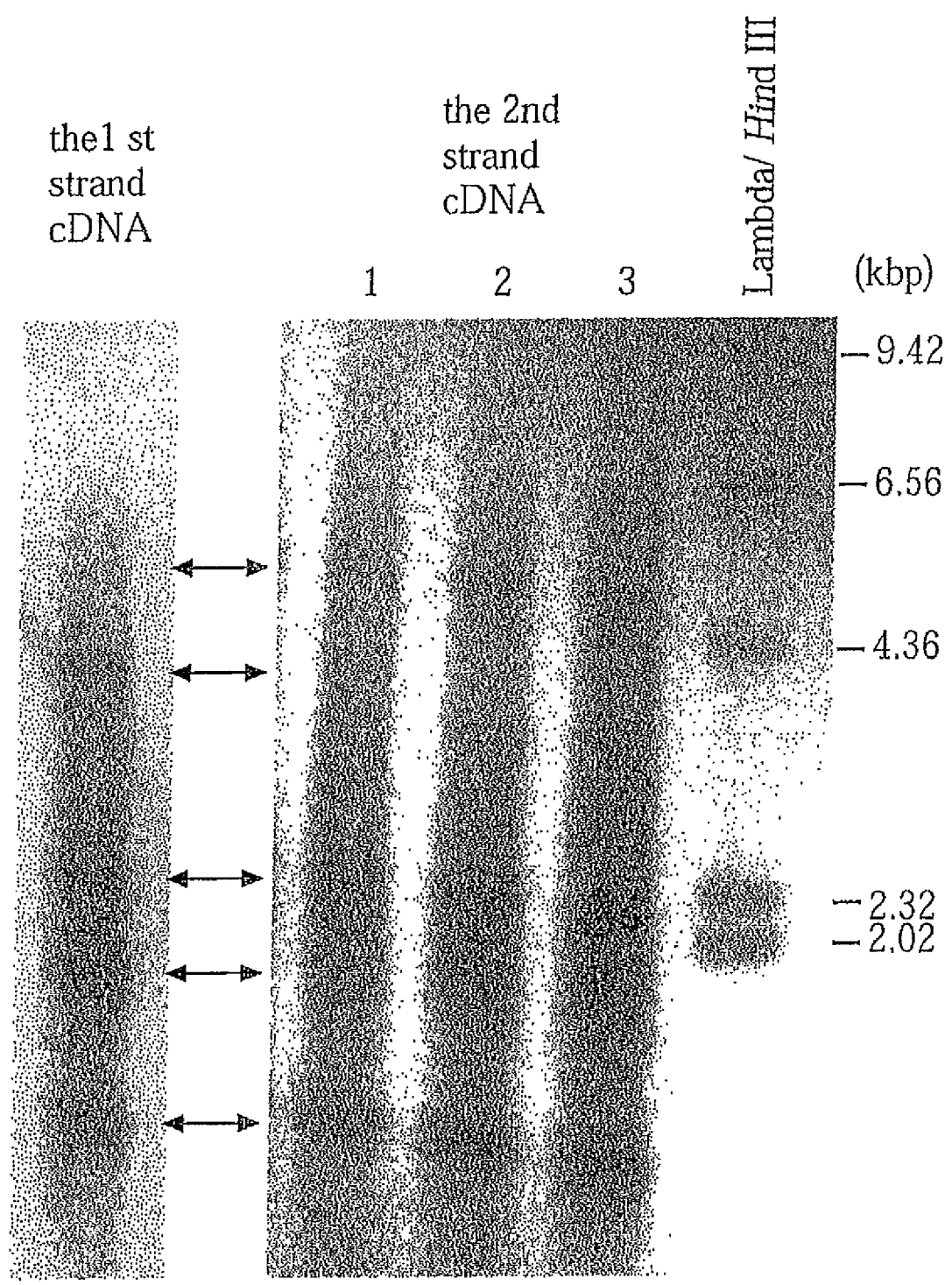

FIG. 4 shows the result of examining the ratio between a linker ligation cDNA of intercellular cDNA and a linker, using linkers with various molar ratios.

A linker combined with 2 µg of $N_6/GN_5$ ($N_6:GN_5=1:4$) was ligated with various quantities of cDNAs (1000 ng for Lane 1, 500 ng for Lane 2 and 200 ng for Lane 3). They were supplied for the second strand cDNA synthesis and analyzed by 0.8% gel electrophoresis. Lane 4 comprises markers.

The individual lane on the left side of the Figure refers to the first strand cDNA.

Figure 5A:
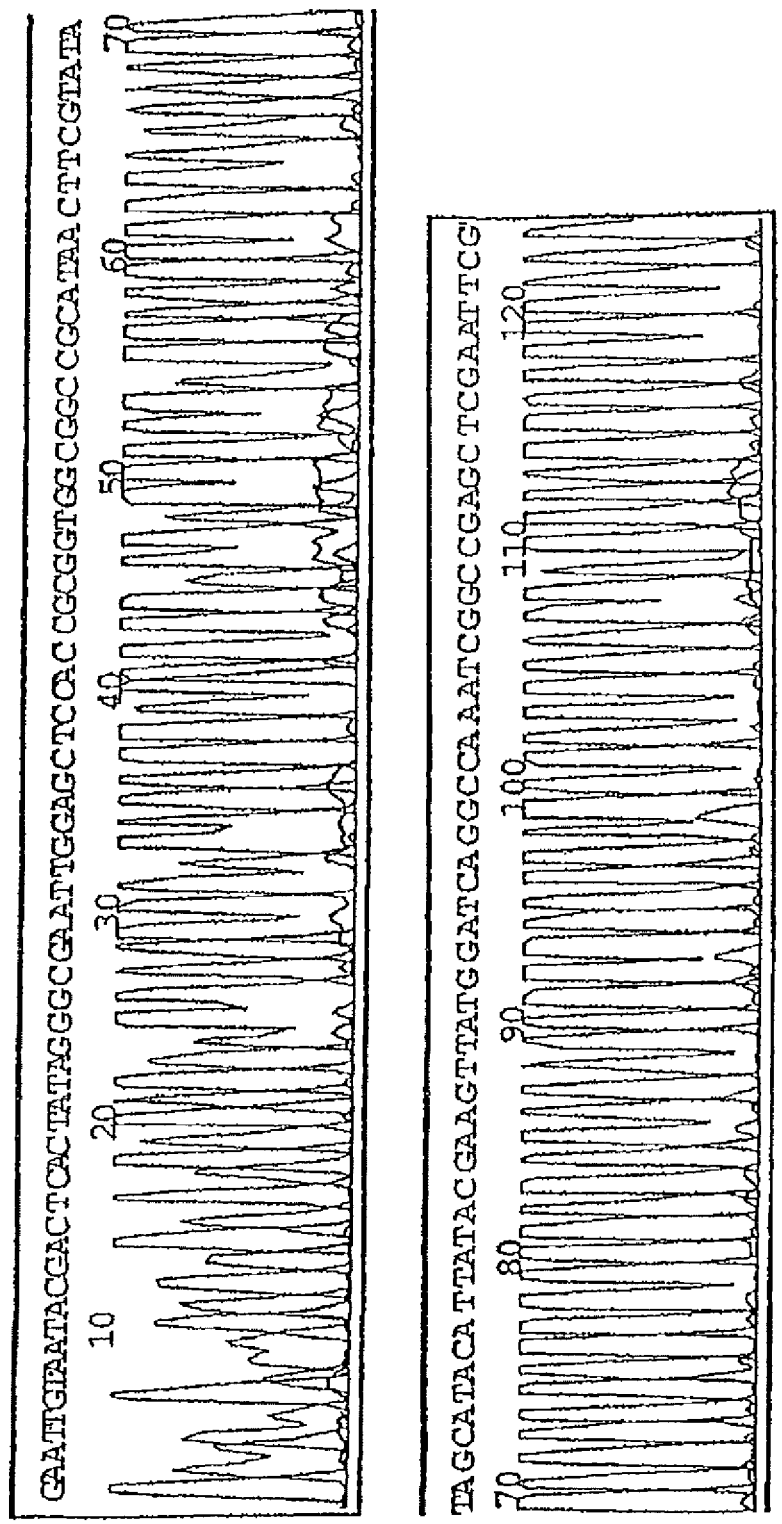
Figure 5D:
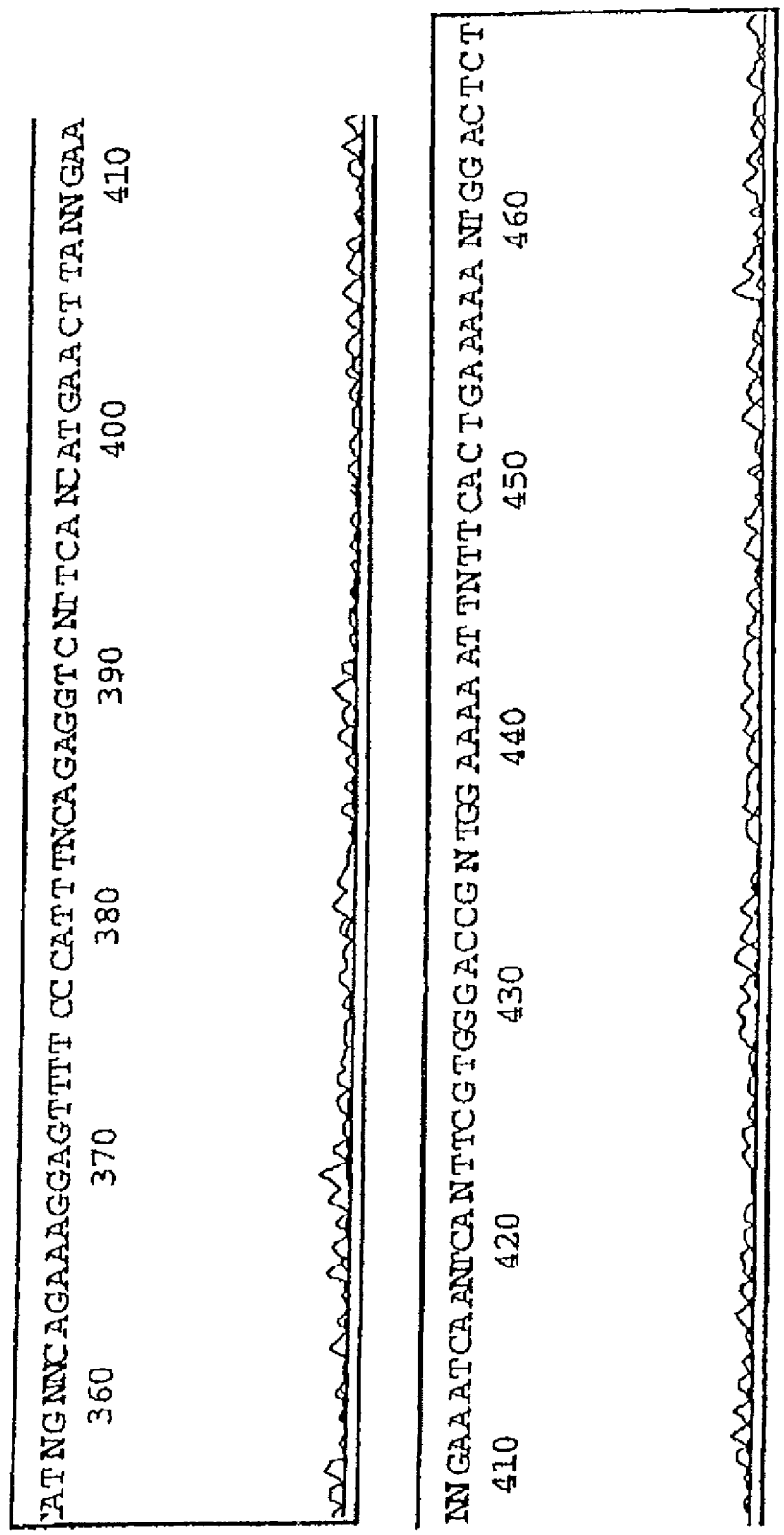
Figure 5E:
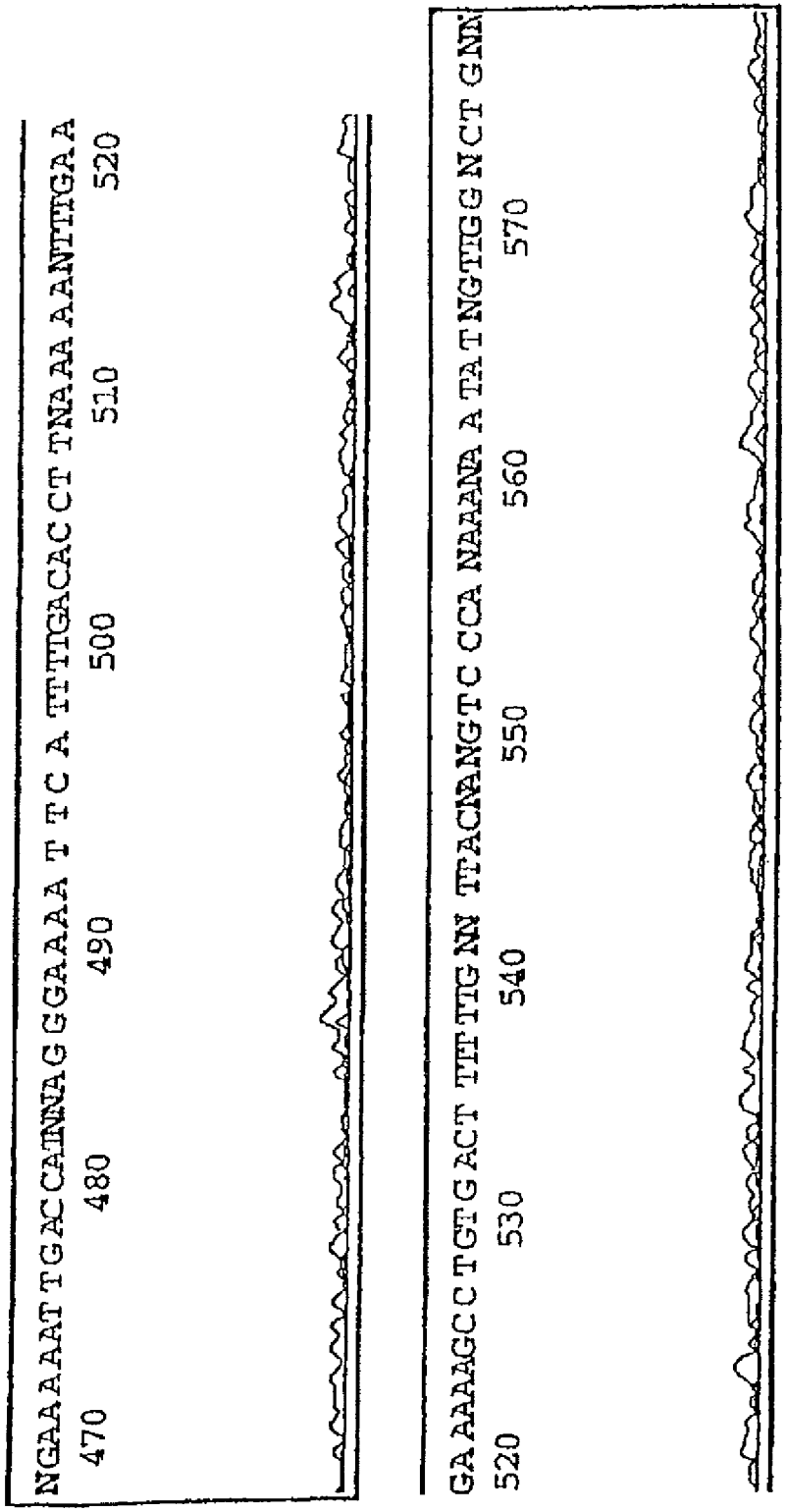
Figure 6A:
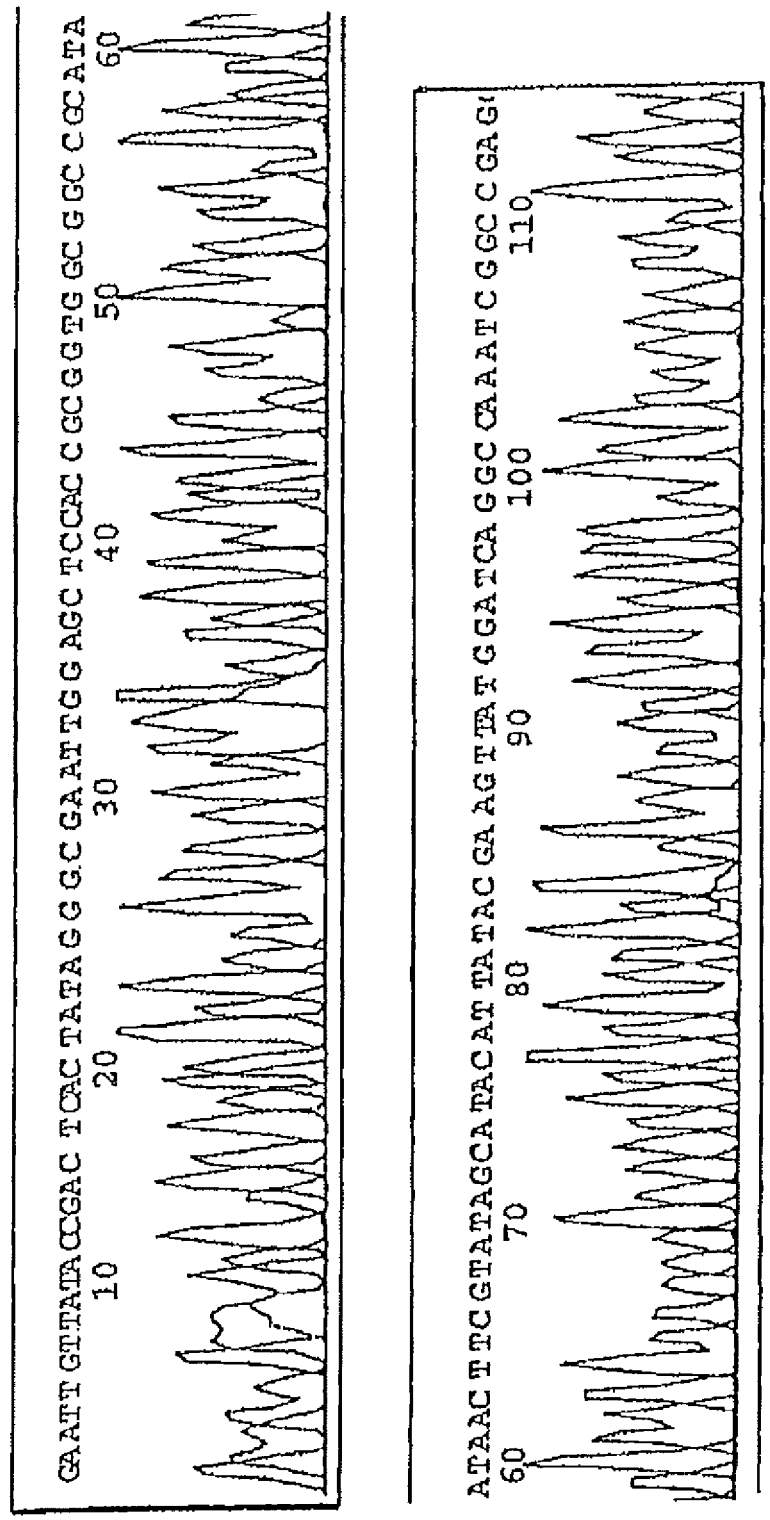
Figure 6B:
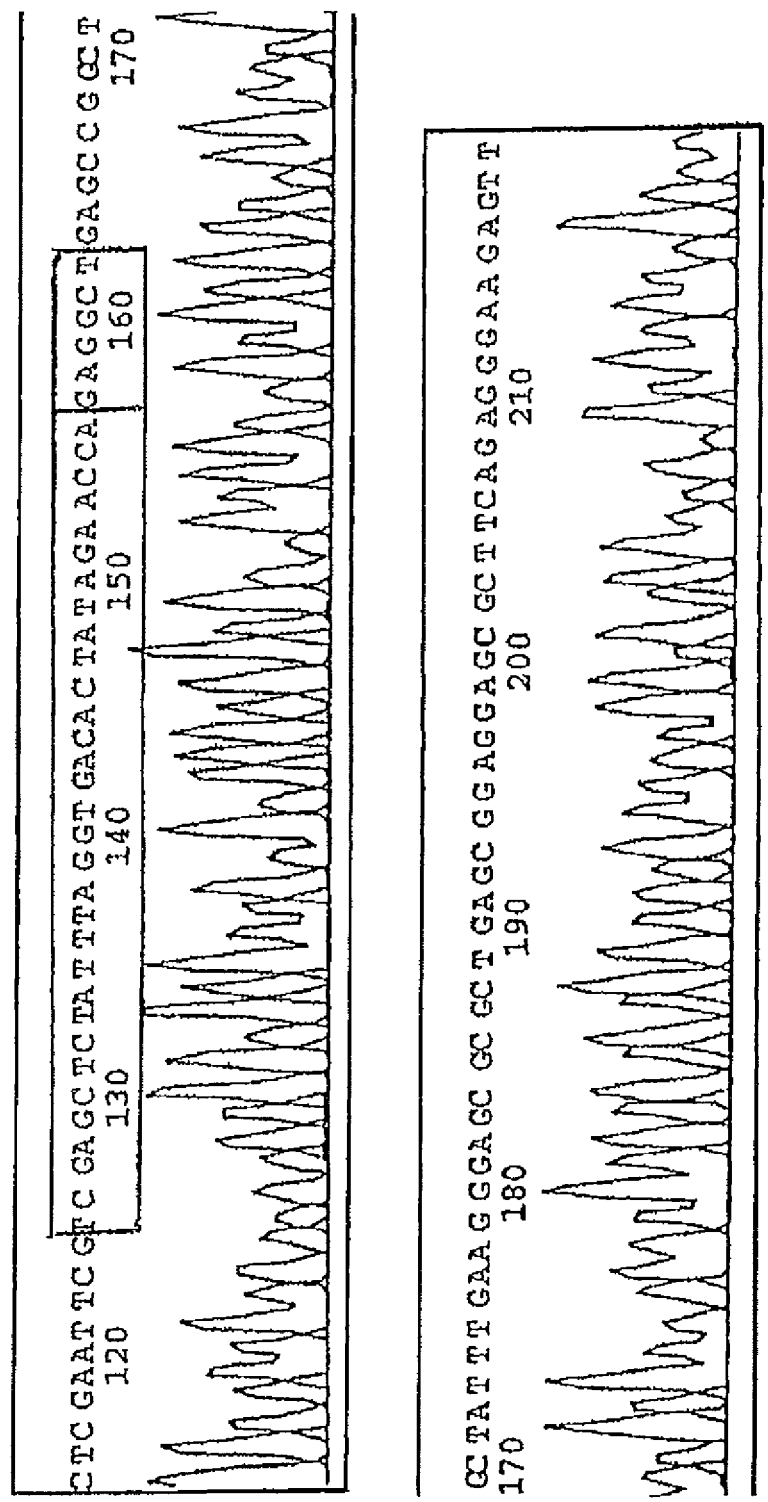
Figure 6C:
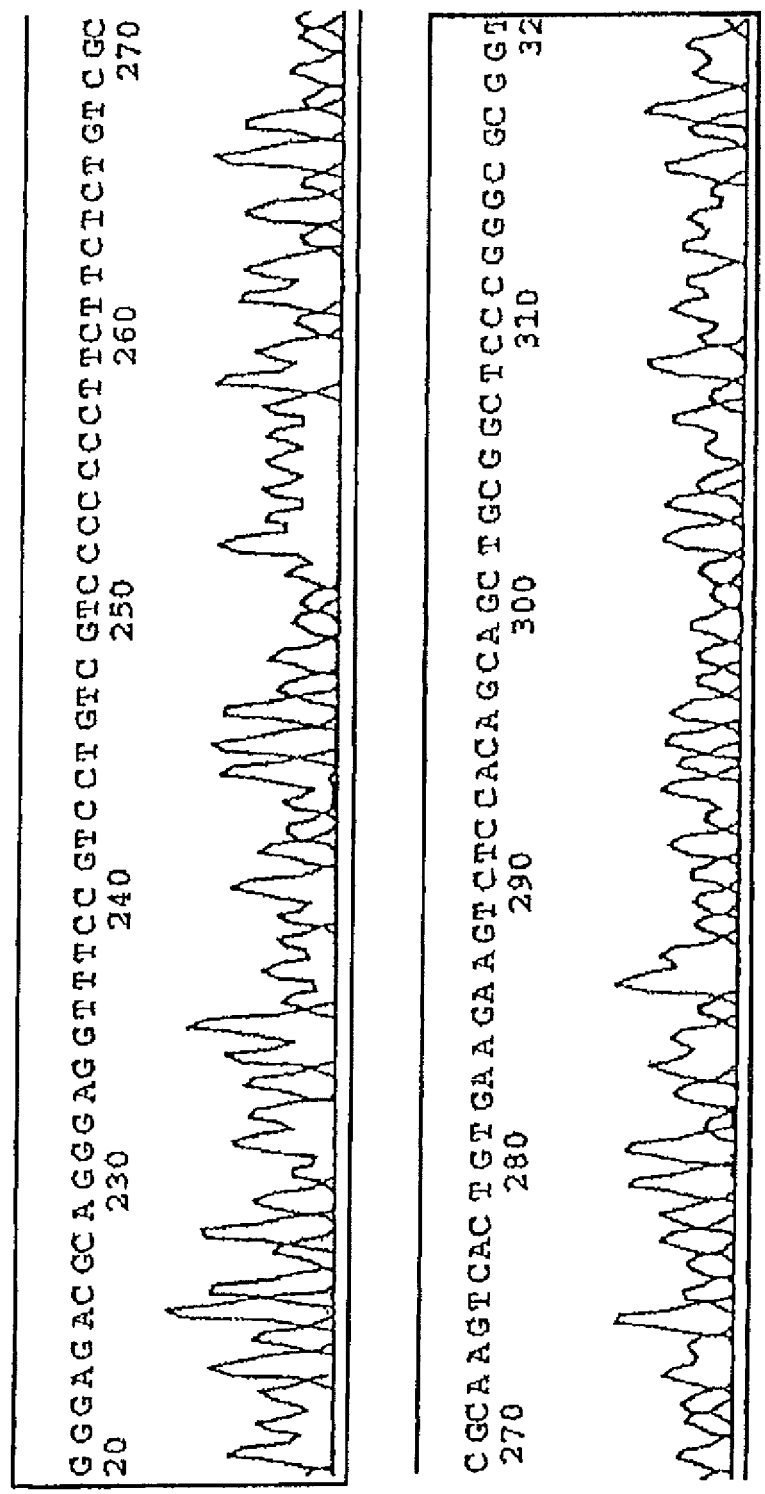
Figure 6D:
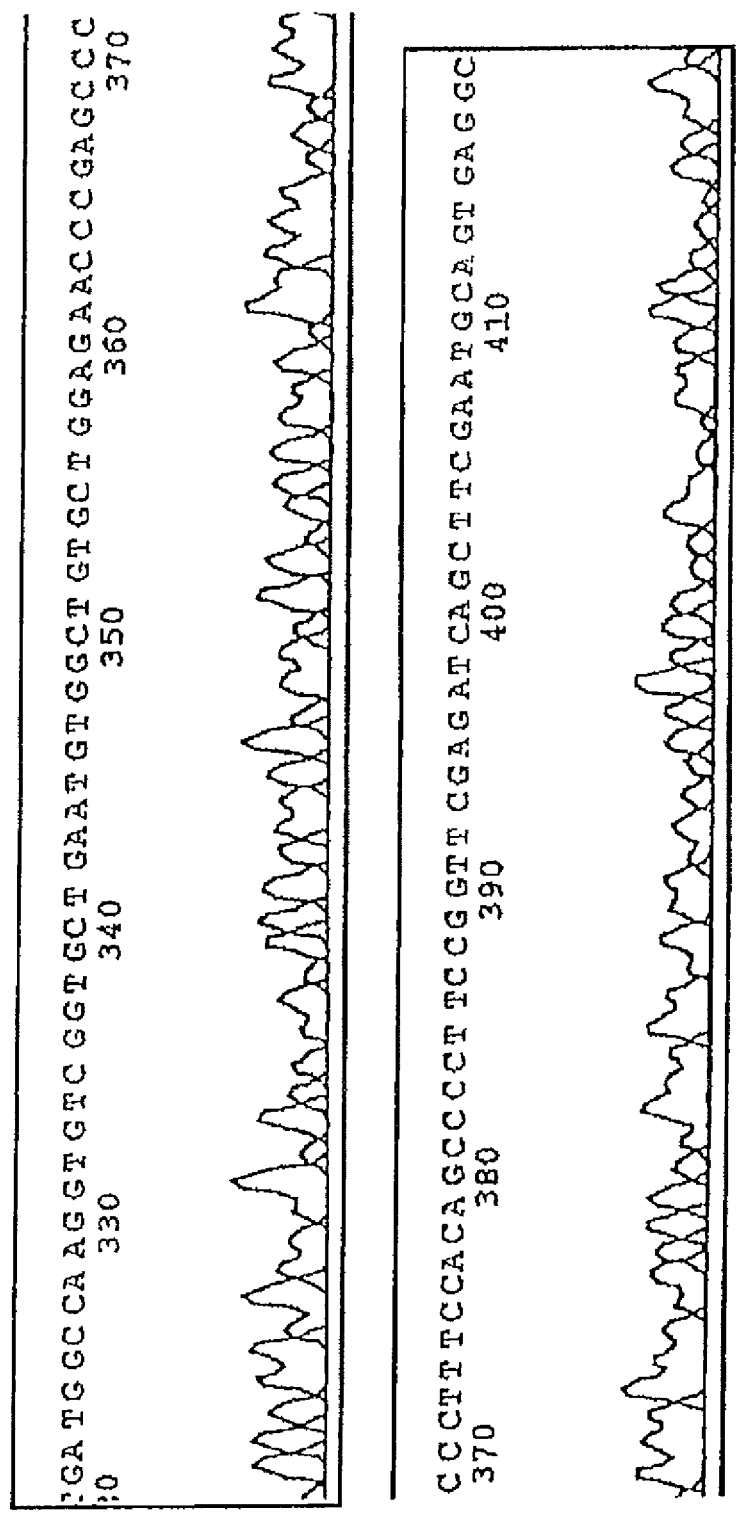
Figure 6E:
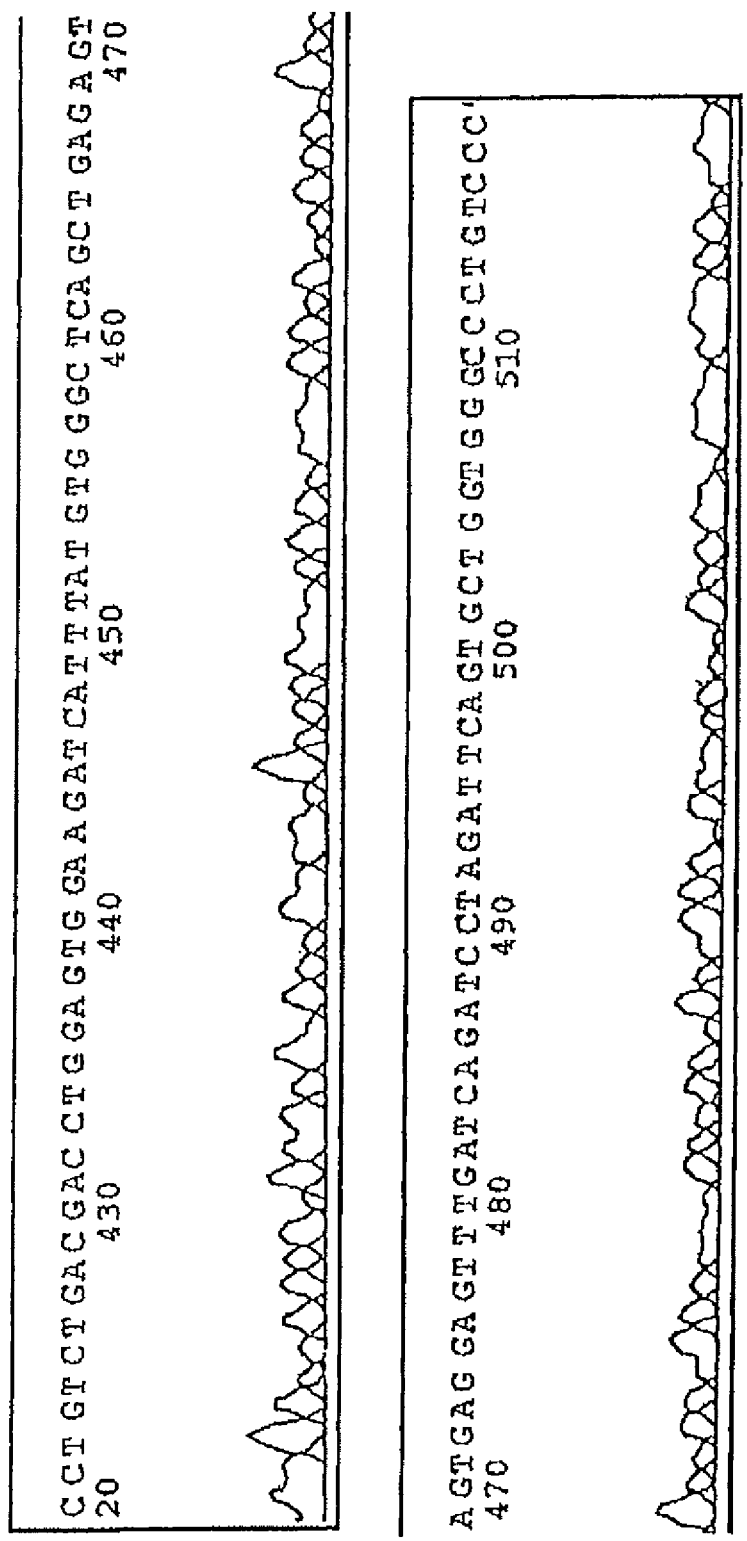
Figure 7A:
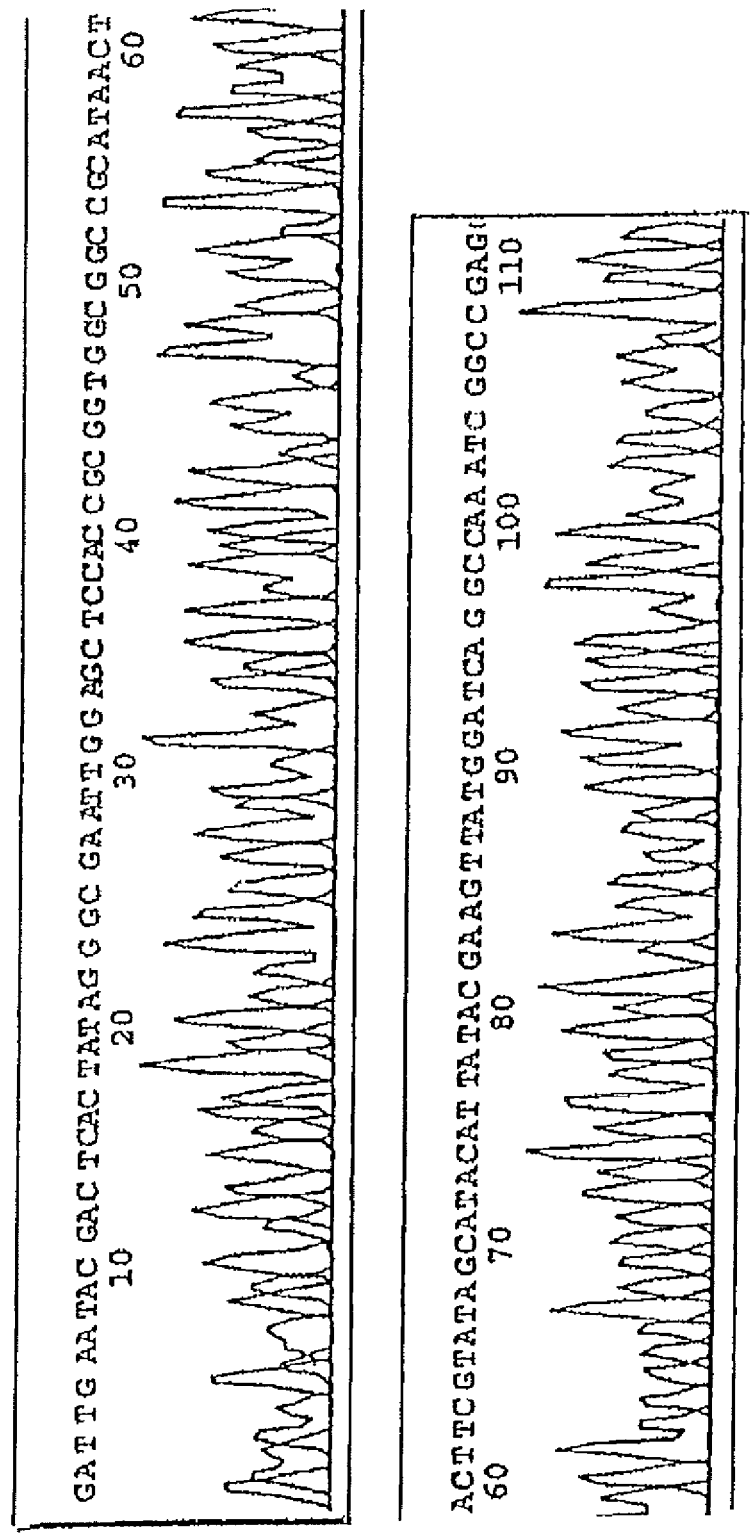
Figure 7B:
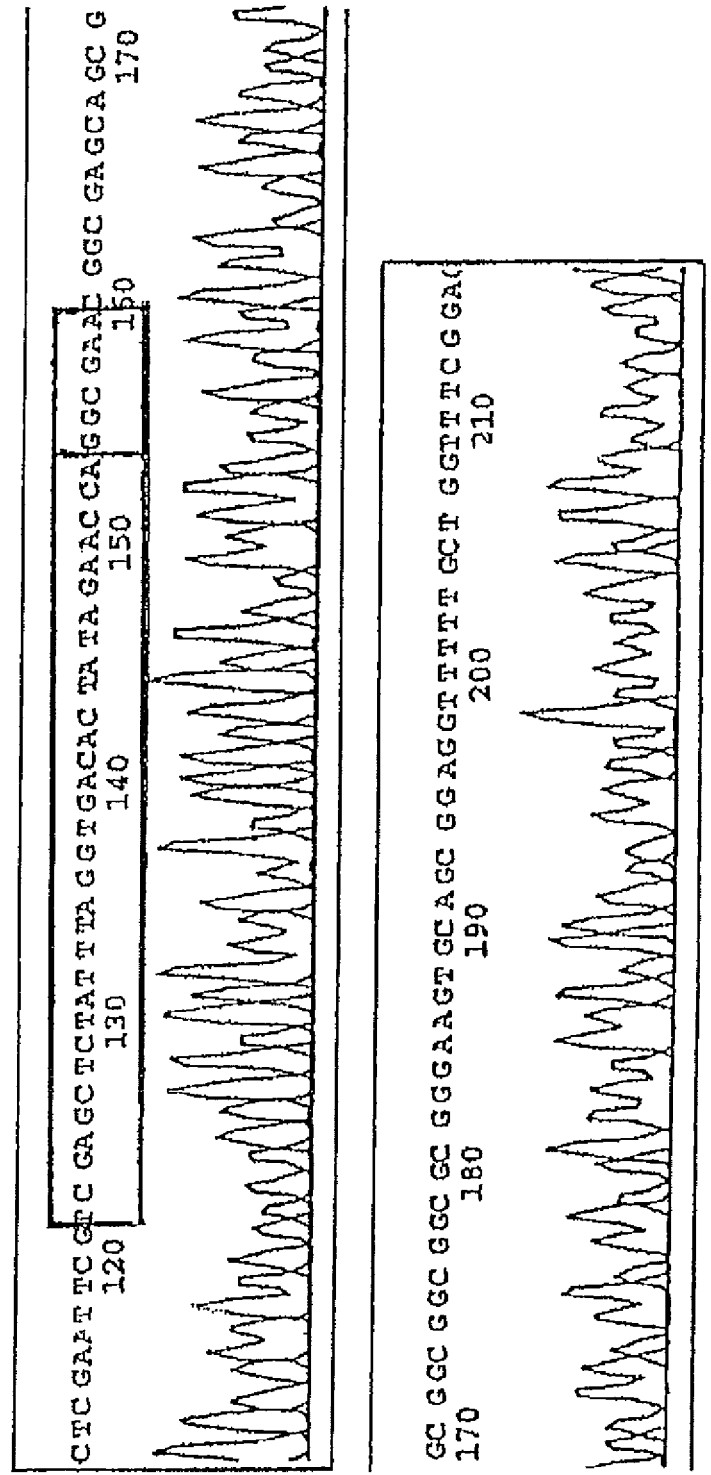
Figure 7C:
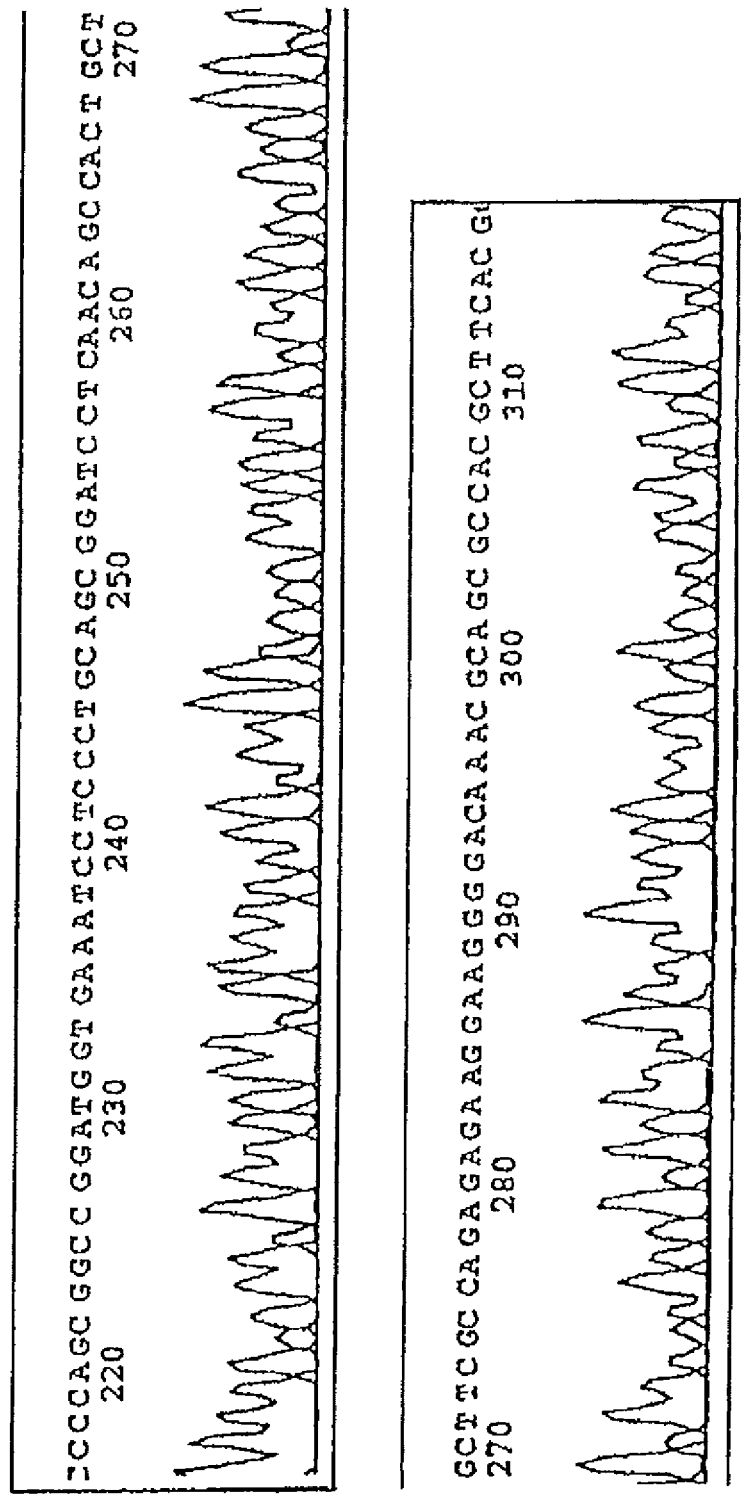
Figure 7D:
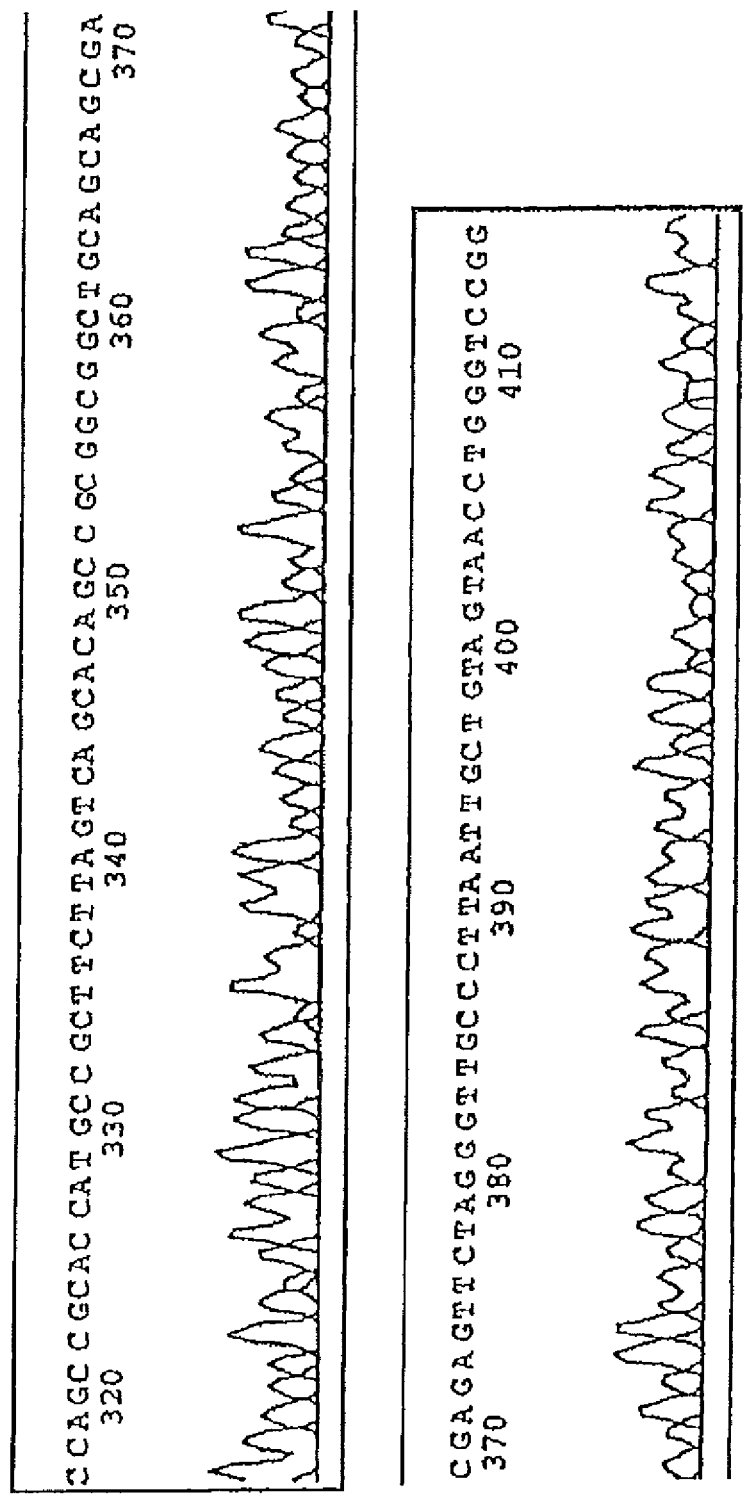
Figure 7E:
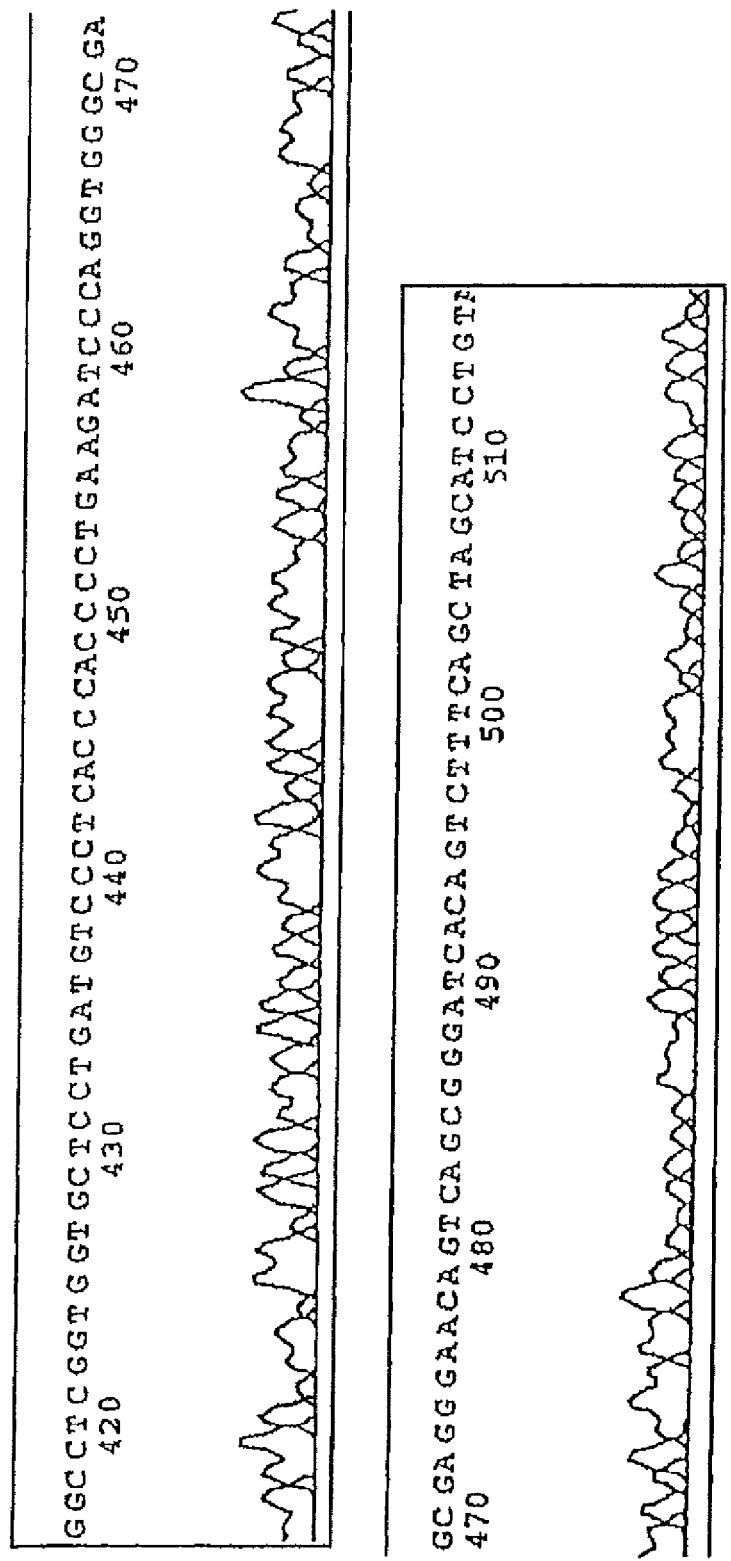

FIG. 5 (SEQ ID NOS: 18-22) shows a sequencing chart of a cDNA sequence having G-tail described in the prior art.

In the presence of a repetition of C in the second strand cDNA (introduced with the G-tail in the first strand), the efficiency of sequencing dropped down as shown in the chart.

FIG. 6 (SEQ ID NOS: 23-27) shows a sequencing chart of a cDNA sequence ligated with a $N_6/GN_6$ linker mixture (proportion 1:4). The sequenced clone D05_042_2-5F-ab2 in FIG. 6 corresponds to the sample 2.05 in Table 1.

FIG. 7 (SEQ ID NOS: 28-32) shows a sequencing chart of a cDNA sequence ligated with $GN_5$ linker. The sequenced clone G07_052_3-7F.ab1 in FIG. 7 corresponds to the sample 3.07 in Table 1.

Figure 8:
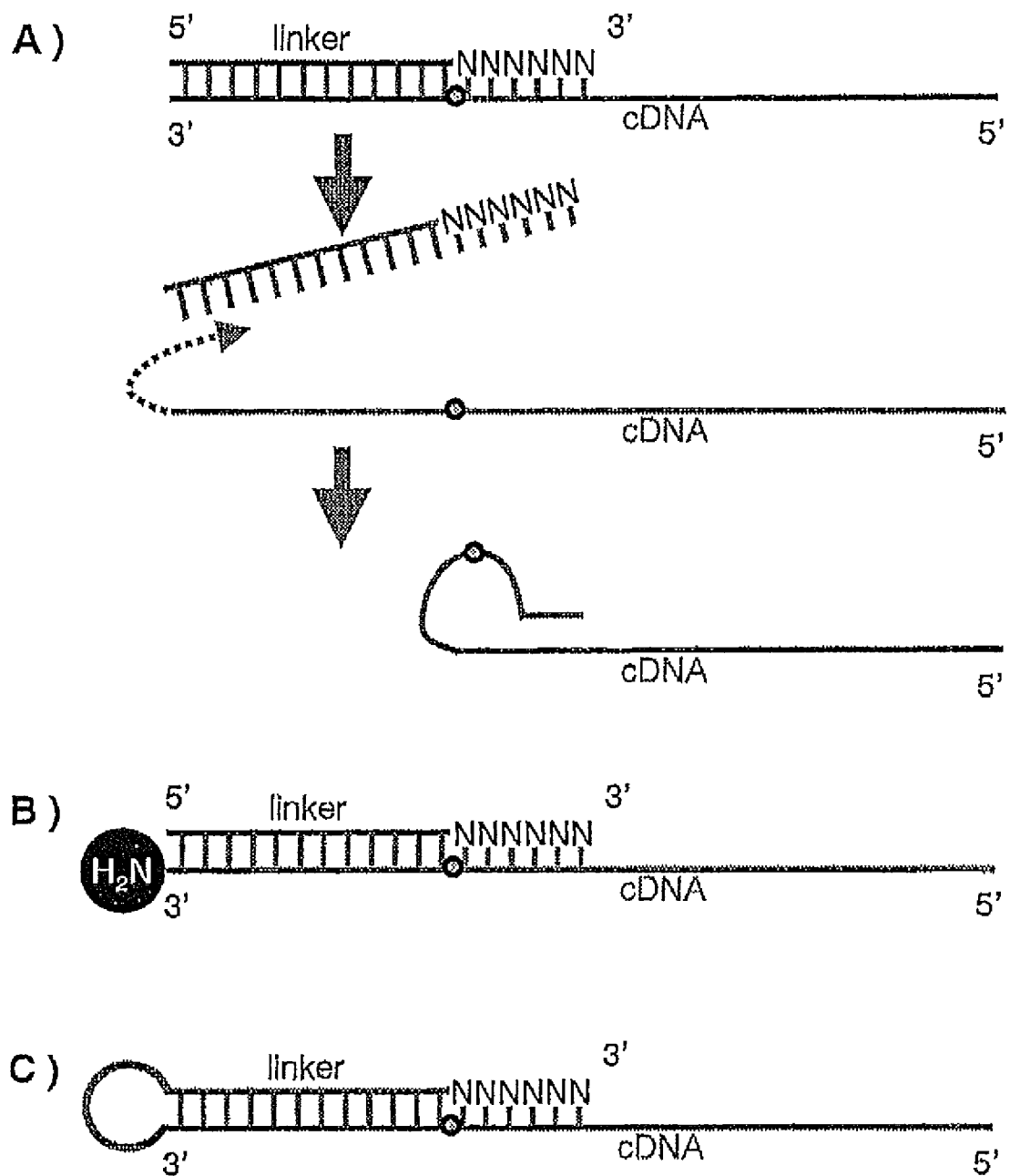

FIG. 8 schematically shows a loop bias and the possible solutions. In FIG. 8(A), the biases are explained. One of the end of the fixed or constant portion of the single strand linker, after removal of the other single strand from the double strand linker, may interact with the single strand cDNA to form a loop and block the following synthesis of the second strand cDNA.

As shown in FIG. 8(B), $NH_2$ as a protecting group is bound to the 3' end in the case of one end of the constant or fixed lower strand. There is no possibility of forming a loop, and so the second strand cDNA synthesis is not inhibited.

In FIG. 8(C), the 3' end of the fixed or nonvariable second strand (lower strand in the figure) and the 5' end of the fixed or nonvariable first strand (upper strand in the figure) of a linker are bound together to form a loop. This prevents the possibility of forming a loop with a single strand cDNA, and so the second strand cDNA synthesis is not inhibited.

DETAILED DESCRIPTION OF THE INVENTION

The present invention solves the above-mentioned problems in the prior art by providing a linker and a population of linkers comprising an oligonucleotide fixed portion and an oligonucleotide variable portion. Such a linker and a population of linkers can bind to an end of a target single strand polynucleotide or a population of target polynucleotides, as well as allow second polynucleotide strand synthesis.

According to an embodiment of the present invention, a linker and a population of linkers comprising an oligonucleotide fixed portion and an oligonucleotide variable portion are provided. The fixed portion is preferably an oligonucleotide portion which is nonvariable in any linker of a population of linkers. The linker fixed portion can be a single stranded or double stranded oligonucleotide, preferably, a double stranded oligonucleotide. The fixed portion preferably comprises at least one of the following: a restriction site, a recombination site, a polymerase promoter site, a marker or a tag.

The variable portion is preferably synthesized at random. The linker of the resulting population of linkers has a nonvariable portion, preferably the common portion among the population, and a variable portion which is different for each linker among the population.

The population of linkers according to the present invention may comprise, as a variable portion, one or more linkers having an oligonucleotide sequence specific for the 3' or 5' end of a target single strand polynucleotide. Said oligonucleotide sequence is specifically selected in order to bind and isolate one or more specific target polynucleotides among a population of target single strand polynucleotides.

The linker variable portion according to the present invention may also work as a primer in the synthesis of a second strand polynucleotide, as for example a long strand fidl-coding or full-length cDNA.

Said randomly variable single strand oligonucleotide portion can comprise any kind of nucleotide. Preferably, the variable portion has the formula (N)n, wherein N is A, C, G, T or U, or their derivatives, and n is equal to or higher than 1. When the integer n is equal or higher than 2, the nucleotides of the variable portion may be the same or different from each other.

The integer n is advantageously is from 1 to 10, preferably from 4 to 8, more preferably n is 5 or 6.

As one method, in the variable portion the first to third nucleotides (beginning counting from the side of the fixed portion to the free end as shown in FIG. 2) of (N)n can be G. A mixture having different strand length (that is, the length of n), and presence or absence of G is also within the object of the present invention. Preferably, the mixture is a mixture of $N_6/GN_5$ with different proportion and the proportion is preferably 1:4.

The present invention further relates to a linker-polynucleotide product comprising the linker according to the present invention and a single stranded or double stranded polynucleotide annealed and/or ligated to the variable portion of said linker, and to a vector comprising said linker-polynucleotide product.

Preferably, said single or double stranded polynucleotide is a long strand, full-coding/full-length cDNA.

Accordingly, the present invention discloses a method for the preparation of linker-polynucleotide products or polynucleotide libraries comprising the linkers according to the present invention annealed and/or ligated to target single stranded polynucleotides.

The present invention further relates to a method for the preparation of polynucleotide products or libraries comprising the linkers according to the invention annealed/ligated to a double stranded polynucleotides, preferably, to a method for the preparation of long strand, full-coding length cDNA libraries.

The present invention further relates to a method for marking polynucleotide libraries by providing a linker population according to the invention comprising a marker in the fixed portion. This marking system allows to distinguish and recognize libraries of different species (for instance, human, mouse, *Drosophila*, rice, and the like) and it can be used for distinguishing libraries of different tissues (for instance, liver, brain, lungs, and the like) for each species.

According to the present invention, a method for binding a linker and a linker population described below and said linker or linker population with a target single stranded polynucleotide or a population of target single stranded polynucleotides is provided, comprising the steps of:

i) preparing a linker or a population of linkers comprising an oligonucleotide fixed portion and an oligonucleotide variable single stranded portion;

ii) annealing a target single strand polynucleotide(s) to the variable portion(s) of said linker.

Hereinafter, in some cases, the present invention, for simplicity, will be described for a population of linkers (also indicated as a population of linkers or simply linkers) as well as to a method for binding said population to target polynucleotides and to a method for synthesizing double strand polynucleotides. However, it is clear that the present invention also includes the individual linkers making up said population of linkers and a method comprising the use of such individual linker.

The fixed portion of each linker in the population of linkers according to the present invention can be a single or double stranded oligonucleotide.

Preferably, the fixed portion, as well as the linker, is a double stranded oligonucleotide, accordingly, the method comprises the steps of:

i) preparing a linker or a population of linkers comprising an oligonucleotide double stranded fixed portion and oligonucleotide variable single stranded portion, wherein said variable portion is protruding outside said double stranded fixed portion (therefore, the variable portion forms a cohesive protruding end);

ii) annealing a population of target single stranded polynucleotides to the variable portions of the population of linkers, and preferably ligating the annealed end of said target single stranded polynucleotides to the adjacent fixed portions of linkers (see steps (F) to (G) in FIG. 2).

Said linker or linkers can be prepared with any methodology known in the prior art, for example, with one oligonucleotide strand having the direction 5'-3', comprising a fixed nucleic acid sequence at the 5' portion and a variable nucleic acid sequence end at the 3' portion. Then, the other oligonucleotide strand comprising a fixed nucleic acid sequence is prepared. Finally, the fixed portion of one strand and the fixed portion of the other strand are annealed so that the variable portion of one strand protrudes outside the double strand fixed portion. As a matter of course, the linker can also be prepared with an inverted order of steps and with other methodologies.

When the linker according to the present invention is a double stranded linker, for the purpose of the present application, the strand comprising the fixed portion and the variable portion is also referred to as "the first strand", while the other strand complementary to the fixed portion of the first strand is referred to as the "second strand".

The present invention further relates to a linker comprising only one oligonucleotide strand comprising a fixed portion and a variable portion (that is only comprising the "first strand" and not comprising the "second strand"). If the linker has the direction 5'-3', the variable portion of the end of this single stranded oligonucleotide anneales to the 3' end of a target single stranded polynucleotide. Then, the second strand polynucleotide, complementary to this target single stranded polynucleotide, is synthesized.

One or more linkers can also be prepared in such a way that the strand comprising a variable portion has a direction 3'-5'. As a result, the variable portion is positioned at the 5' end. The 5' end variable portion of the linker thus prepared anneals to the 5' end of the target polynucleotide. If the other strand is present, it can be ligated to the 5' end of the target polynucleotide.

The present invention also provides a method for preparing linker-polynucleotide products comprising the linker or the population of linkers according to the present invention and a double stranded polynucleotide, comprising the steps of:

i) preparing a population of linkers comprising an oligonucleotide double stranded fixed portion and an oligonucleotide variable single stranded portion, wherein said variable portion is protruding outside the double stranded fixed portion (therefore, the variable portions form cohesive protruding ends);

ii) annealing a population of the target single stranded polynucleotides to the variable portions of said population of linkers, and ligating said population of target single stranded polynucleotides to the adjacent (second strand) fixed portions of said linkers; and iii) synthesizing second single stranded polynucleotides, complementary to the target single strand, by using the variable portions as primers.

The polynucleotide sequence can also be prepared using only one strand of the linker according to the present invention. In this case, a method of the invention comprises the steps of:

i) preparing a population of single stranded linkers comprising an oligonucleotide fixed portion and an oligonucleotide variable single stranded portion;

ii) annealing a population of the target first strand polynucleotides to a variable portion of the population of linkers;

iii) synthesizing second single stranded polynucleotides, complementary to the target first strand, by using the variable portions of linkers as primers.

The fixed oligonucleotide portion of the linker or population of linkers can be any oligonucleotide sequence. This fixed sequence is preferably a nonvariable portion and it is therefore the common for all of the linkers of the same population. This fixed portions can also comprise oligonucleotide sequences consisting of one or more groups and therefore the fixed portions, in this case, can show some differences among the same population. However, since these oligonucleotide sequences consisting of one or more optional groups will not change the general structure of the fixed portions, for the purpose of the present invention, the fixed portion, comprising or not comprising the variable oligonucleotide sequences consisting of one or more groups will be, for simplicity, indicated as a "fixed" portion.

The fixed portion can be a nonvariable portion even in a population of linkers. That is, it can be the same one for any linkers comprising the population.

The fixed portion can be any oligonucleotide sequence (DNA or RNA), and it is preferably the same or almost the same for the linker or the population of linkers used in any specific experiment or for a specific library.

The linker fixed portion can therefore be intended both as a single or double stranded oligonucleotide, preferably, it is a double stranded oligonucleotide. In this case, the single stranded variable portion constitutes a protruding end. The variable portion can act as a primer in a second strand polynucleotide synthesizing process.

The fixed (or nonvariable) portion preferably comprises one or more restriction sites, homologous recombination sites, polymerase promoter sites, a marker and/or a tag. Preferable restriction sites are, for example, BamHI, XhoI, SstI, SalI or NotI and others, for example those disclosed in Hyone-myong Eun, Chapter "Restriction endonucleases and modification methylases".

Examples of homologous recombination sites are attB, Gateway™ (Life Technologies), Cre-lox (Qinghua Liu, et al., 1998, Current Biology, 8:1300-1309) and Flp/FRT (J. Wild, et al, 1996, Gene, 179:181-188).

Further, as for the polymerase promoter site, it can be a RNA polymerase promoter site, for example one of those described in Hyone-Myong Eun, page 521. Preferably, it can be T3, T7, SP6, K11 and/or BA14 RNA polymerase promoter site.

A marker can be any sequence or sequences of nucleotides, for example a sequence specific for a particular tissue or species.

As a tag, any group or molecule able to be bound to an end of the fixed portion of one strand or the other strand of a linker can be used. In fact, when a single strand of the linker is removed, for example by increasing temperature, the end of the other single strand could form a loop with the target single stranded polynucleotide (FIG. 8). Preferably, a protecting group is bound to the 3' end of the strand consisting of only this fixed portion in order to avoid that the end of the strand consisting of only the fixed portion forms a loop with the target single strand polynucleotide mainly ligated to this strand, which inhibits the synthesis of the second strand polynucleotide (FIG. 8A). Therefore, any group that does not have a 3'—OH and cannot be ligated nor extended by DNA polymerases can be used for the purpose of the present invention.

As a protecting group, for example ddNTPs can be used. Preferably, a $NH_2$ group is also used as a protecting group (FIG. 8B).

As a further particular solution, in order to avoid the problem of loop bias, both ends can be bound together so that the ends of both strands of the fixed portion of the linker positioned opposite to a variable portion form a loop (FIG. 8C). With this solution, the ends of the fixed portion cannot form a loop with the target single stranded polynucleotide, and the synthesis of the second strand polynucleotide is not inhibited.

The oligonucleotide variable portion of the linker or the population of linkers is, preferably, randomly synthesized. Accordingly, in a population of linkers, the variable portion of any linker is preferably synthesized at random and the sequence of the variable portion and/or the number of bases in each linker differs from each other. A population of linkers, therefore, comprises protruding ends having a high number of different sequences. Such a population of linkers comprises a high variation of random protruding ends. These recognize, anneal and/or ligate to the complementary ends of a population of target single stranded polynucleotides. That is, this is a population of full-length cDNAs forming polynucleotide sequences comprising the linker and a target single stranded polynucleotide (see FIGS. 1 and 2).

The present invention therefore also relates to a population of linkers comprising at least two linkers prepared according to the present invention. Preferably, the invention relates to a population of linkers comprising at least two subpopulations of linkers.

The population of linker can be that one in which the fixed portions in all of the linkers are an oligonucleotide portion having the same sequence. The population of linkers may also comprises two or more subpopulations of linkers, wherein one subpopulation of linkers comprises linkers in which the fixed portion is an oligonucleotide portion having the same sequence, and other subpopulations that differ from each other in the fixed portion sequence.

Preferably, in the population or subpopulation of linkers the variable portions of the linkers are synthesized at random. Preferably, in the population or subpopulation, the sequence of the variable portions of the linkers are different from each other.

The variable portion can also be a specific oligonucleotide sequence complementary for an end (preferably 3' end) of a target single stranded polynucleotide.

Preferably, the linker population of the present invention includes among the variable portions one or more specifically determined portions able to recognize and anneal to the end(s) of specific target polynucleotides which are intended to be selected from the population of target polynucleotides.

The end of a target single stranded polynucleotide anneals to the protruding variable end of the linker. When a population of linkers is added to a population of target single stranded polynucleotides, the variable portions (protruding ends), preferably randomly synthesized, in the linkers recognize and anneal to the ends of the population of target single stranded polynucleotides.

Preferably, the linkers according to the invention are double stranded oligonucleotides comprising a fixed portion (preferably a nonvariable portion for all the linkers of a population) and a variable portion, which is different for any linker of the population. According to the first embodiment, the 3' end of the target single strand polynucleotide anneals to the 3' end of protruding end of the variable portion and ligates to the 5' end of the fixed portion of the other strand adjacent to the 3' end of said target single stranded polynucleotide.

The linker can also be constituted, according to a second embodiment, by the fixed portions of one strand having the direction 3'-5' and the other strand. In this case, the 5' end of the target single stranded polynucleotide anneals and ligates to this variable portion of the linker.

The variable single stranded oligonucleotide portion of the linker can comprise any kind on nucleic acid. Preferably, said variable portion has the formula $(N)n$, wherein N is A, C, G, T or U or their derivatives and n is equal to or higher than 1, and if n is an integer equal to or higher than 2, the nucleotides (N) of the variable portion may be the same or differ from each other. Preferably, $1 \leq n \leq 10$ and more preferably $4 \leq n \leq 8$. As a particular preferred linker, n is 5 or 6, that is, $N_6$ or $N_5$.

The first, second and/or third N, closest to the fixed portion (that is, the nucleotides of the variable portion coming from the 5' end of the linker in case of the first embodiment) can also be a G, according to the formula $(G)_m(N)_{n-m}$, wherein m=1 to 3. Preferably, the linker variable portion can be $GN_4$, $GN_5$, $G_2N_3$, $G_2N_4$, $G_3N_2$, $G_3N_3$, $N_5$, $N_6$ or a mixture thereof.

More specifically, the linker population according to the present invention is a mixture of $(N)_n$ linker and $(G)_m(N)_{n-m}$, preferably $N_6/GN_5$, $N_6/G_2N_4$ or $N_6/G_3N_3$ having different proportion. The proportion of the $N_6/GN_5$ linkers in the mixture can be 0:1-1:0, preferably 1:3-1:5, more preferably 1:4. The ligation can be realized with any ligation method known in the prior art, preferably by using a DNA ligase, more preferably a T4 DNA ligase or E. coli DNA ligase (see for example, Hyone-Mong Eun, in the chapter "Ligases") or using a RNA ligase (Maruyama et al, 1995).

Preferably, the ligation reaction according to the present invention includes the addition of ligase stimulating agents. Preferably, as a ligase stimulating agent, polyethylene glycol (PEG), preferably at 6000-8000 molecular weight, is used.

After the annealing and/or ligation step, the variable linker portion (that is, the protruding or free 3' end of the linker of the first embodiment) can act as a primer for the synthesis of a second strand polynucleotide, forming a polynucleotide sequence comprising the linker according to the invention and a double stranded polynucleotide.

The ligation of the linker according to the invention to a target single stranded polynucleotide can also be realized by using the oligo-capping technique (K. Maruyama et al., 1995, Gene, 138:171-174; and S. Kato et al., 1995, Gene, 150:243-250). The oligo-capping method essentially comprises the following steps: i) mRNAs extracted from cells are treated with a phosphatase enzyme, preferably bacterial alkaline phosphatase for removing phosphates from non full-length mRNAs (that is, forming 5' ends of uncapped RNA having an hydroxyl at the 5' end, but not removing the CAP structure from the capped full-length RNA); ii) the mixture obtained in i) is treated with a pyrophosphatase, preferably tobacco acid pyrophosphatase (TAP), which removes the CAP structure from full-length mRNAs and leaves the full-length 5' ends with a phosphate group; iii) the full-length mRNA having a phosphate group at the 5' end is ligated to a specific RNA or a DNA adapter with a RNA ligase; and iv) an oligo dT is added and the complementary strand is synthesized.

The method for binding the linker according to the present invention to a target polynucleotide and/or the method of preparing a polynucleotide sequence according to the present invention can also be performed using, as a ligation step, a modified oligo-capping method as follows.

Accordingly, a target single stranded polynucleotide (which can be RNA, mRNA prepared as described by the oligo-capping method, or cDNA) can be ligated to the linker according to the present invention in presence of a ligase.

In particular, when the linker of the present invention is a double stranded linker, an end of the target single stranded polynucleotide ligates to the second strand (which consists of the only fixed portion) and anneals to the variable portion of the first portion of the linker.

As another possibility, the target polynucleotide ligates to the variable portion of the linker (which can be either a single or a double strand). In both cases, an oligo dT is added and a complementary polynucleotide, preferably cDNA, is synthesized.

The use of RNA ligase is not limited to RNA or mRNA as above described, but can also be used to ligate DNA.

The ligation method using RNA ligase in order to bind the linker according to the present invention and a target single stranded polynucleotide, can therefore bind:
i) a single stranded DNA to a single stranded DNA; ii) a single stranded RNA to a single stranded RNA; and iii) a single stranded DNA to a single stranded RNA or a single stranded RNA to a single stranded DNA.

According to an embodiment, the polynucleotide is a long strand, full-coding/full-length mRNA and the linker is DNA (but can also be RNA) and comprises a first restriction enzyme site.

Accordingly, a method is provided for the preparation of a single or double stranded cDNA comprising the steps of:
(I) providing a long strand, full-coding or full-length mRNA comprising a poly-A;
(II) providing a double stranded linker comprising a first restriction enzyme site;
(III) ligating the 5' end of the mRNA (by using a ligase, for instance RNA ligase) to the fixed portion of the second strand of the linker and annealing the 5' end to variable portion of the first strand of the linker;
(IV) providing an oligo dT-primer comprising a second restriction enzyme site, and annealing the oligo dT-primer to the poly-A of the mRNA;
(V) synthesizing the cDNA by addition of a reverse transcriptase and NTPs; during this step, the newly synthesized cDNA displaces the linker first strand (that one comprising the fixed and the variable portion);
(VI) removing the mRNA and obtaining a single stranded cDNA.

Further, a primer can be added to the 3' end of the cDNA, and in presence of a polymerase a complementary DNA is synthesized forming a double stranded cDNA. The double strand formed therefore comprises a first restriction enzyme site at one end and a second restriction enzyme site at the other end.

The removal of mRNA at step VI) may be performed by addition of a RNase H or other enzyme which cuts RNA in fragments and removes them, or by addition of alkali (for instance NaOH) according to the methodology known in the art (Sambrook et al, 1989).

The double stranded polynucleotide sequence is then cleaved at the first and second restriction enzyme sites, specifically introduced with the linkers, by using the specific restriction enzymes, resulting in forming protruding ends. The double strand polynucleotide with protruding ends is then inserted in a plasmid or phage expression vector or in a sequencing vector (for example, as described in, for example, Sambrook et al, 1989, Molecular Cloning, Cold Spring Harbor Laboratory; Invitrogen Catalog 1999; Stragene Catalog 1999, etc.). The double strand polynucleotide can also be cloned by site-specific recombination (for example attB-attP) or by blunt-ends methodology (Sambrook et al., 1989).

Examples of phage vectors are lambda-ZAP and lambda-Dash (Stratagene).

The invention, therefore, is also related, but not limited, to a phage or plasmid expression or sequencing vector comprising the polynucleotide sequence according to the present invention.

The single or double stranded polynucleotide according to the present invention is RNA or DNA, or also a DNA/RNA hybrid. Preferably, including a long strand full-coding and/or full-length cDNA. The 3' end of said long strand full-coding/full-length cDNA corresponds to the 5' Cap end of mRNA.

For the purposes of the present invention, the wording "full-length cDNA" means a cDNA comprising the 5' and 3' UTR sequences and the oligo dT-primer (that is, complementary to a mRNA comprising the poly-A). It may also comprise additional sequences for cloning, such as restriction enzyme sites. With a full-coding cDNA, a cDNA sequence comprises at least the start and stop codon. "Long strand cDNA" is understood to be a cDNA sequence which is almost full-coding/full-length, lacking one or few nucleotides at the 3' end (corresponding to the 5' end of mRNA) or at the 5' end if considering a cDNA strand complementary to the cDNA complementary to the mRNA (that is, having the same direction of the gene). Such a stop of the synthesis reaction during cDNA synthesis may be caused by the formation of secondary structure of the mRNA, for example, the level of the Cap structure. However, also fragments of genes, nucleotides, cDNAs, RNA or mRNA are not excluded from the purpose of the application of the present invention.

A DNA/RNA hybrid can be prepared by:
providing a long strand, full-coding or full-length mRNA comprising a poly-A;
(I) providing a double stranded linker comprising a first restriction enzyme site;
(II) ligating the 5' end of the mRNA (by using a ligase, for instance RNA ligase) to the fixed portion of the second strand of the linker and annealing the 5' end to variable portion of the first strand of the linker;

(III) providing an oligo dT-primer comprising a second restriction enzyme site, and annealing the oligo dT-primer to the poly-A of the mRNA;

(IV) synthesizing the cDNA by addition of a reverse transcriptase and NTPs; during this step, the new synthesized cDNA displaces the linker first strand (that one comprising the fixed and the variable portion);

(V) adding an oligonucleotide complementary to the second restriction enzyme site of the oligo dT-primer and ligated this oligonucleotide to the poly-A; an hybrid double stranded polynucleotide is then formed.

The hybrid double stranded polynucleotide can be cleaved by specific restriction enzymes as explained above and inserted into a vector as above.

The target single stranded polynucleotide, which anneals to the variable linker portion and/or ligates to the adjacent fixed linker portion of the linker, can be prepared with any technique known in the prior art.

Preferably, the long strand or full-coding/full-length single stranded cDNAs are prepared according the technique of 5' mRNA Cap trapping, disclosed in Carninci et al., 1996, Genomics, 37, 327-336; Carninci et al., 1997, DNA Research 4:61-66; Carninci et al., 1998, Proc. Natl. Acad. Sci USA, 95:520-4; and Carninci and Hayashizaki, 1999, Methods Enzymol. 303:19-44.

Preferably, all the steps described in the above prior art documents are followed, with the exception that instead of the G-tailing step, the population of linkers according to the invention is provided.

Preferably, the Cap-trapping method described in FIGS. 1 and 2 is used, however, the target single stranded polynucleotide is not limited to that prepared with this technology. For example, other methods of isolation of first strand cDNA such as that described in Edery et al., 1995, Mol Cell Biol, 15:3363-71 or the oligo-capping method (K. Maruyama et al., 1995, Gene, 138:171-174; and S. Kato et al., 1995, Gene, 150:243-250) can also be used.

The target single stranded polynucleotides according to the present invention can also be normalized and/or subtracted (for example, Soares et al., 1994, Proc. Natl. Acad. Sci. 91:9228-9232 and Bonaldo et al., 1996, 6:791-806). The recovered normalized and/or subtracted polynucleotides, preferably cDNAs, more preferably long strand or full-coding/full-length cDNAs, are preferably prepared according to the Cap-trapping technology, and then ligated to the population of linkers according to the present invention, or said isolated cDNAs are first annealed and/or ligated to the population of linkers of the present invention, and then normalized and/or subtracted.

The target single stranded polynucleotide may show a bias due to the formation of a loop or hairpin-loop. For example, the 3' end of a synthesized intercellular cDNA may form a loop with an internal portion of itself, preventing the following annealing and ligation with the linker according to the present invention.

In order to solve this problem, the target single stranded polynucleotide is optionally subjected to high temperature, from 25° C. to up the boiling point of the solution (about 100° C.), preferably at 65° C., and then cooled down, preferably in ice, before annealing and/or ligation with the linker according to the present invention.

As a modified method, the secondary structure can be deleted with chemical agents, such as solutions consisting of NaOH (for example 0.1 N), formamide 50-99% and Urea 6-8M or similar agents known to delete/reduce the secondary structure of nucleic acids or denature the double strand nucleic acids. In this case, such agents must be removed, usually by ethanol precipitation, prior to subsequent enzymatic reactions.

As a further modified method, the target polynucleotide annealed and/or ligated to the linker can be subjected to high temperature (hot stall) in order to remove possibility of hairpin-loop formation. The temperature range is from 25° C. up to the boiling point of the solution (about 100° C.), preferably 65° C.

However, the increase of temperature may remove one strand of the linker (that is, the strand comprising the fixed portion and the variable portion), therefore later the same strand linker or any primer can be added to the other strand of the linker and the polynucleotide sequence comprising the target single stranded polynucleotide. There is a possibility of the formation of hairpin-loop, but it can be avoided using the solutions described in FIGS. 8B and 8C.

Using the method according to the invention, the annealing and ligation steps are very efficient, so that the following cloning step allows the preparation of high-titer libraries without PCR amplification.

The method according to the invention allows the preparation of libraries more advantageously compared to the method in the prior art and in particular to the method of G-tailing.

The G-tailing method in fact has a serious drawback during the sequencing process, as shown in FIG. 5. The second strand cDNA comprises a repetition of C, complementary to the G-tail sequence (the length of which cannot be easily controlled and therefore may reach the length of 20-30 G). This excessive C repetition makes the sequencing process stop, preventing the DNA sequencing.

The method using the linker according the invention does not have this drawback (even if the random variable portion comprises G, they are statistically within a small number) and can allow an efficient sequencing as described in FIGS. 6 and 7.

The clone of FIG. 6 comprises a portion of a linker N6 (marked in the box of FIG. 6) corresponding to nucleotides 12 to 49 of SEQ ID NO:3. The nucleotides 1 to 11 (included) were cleaved as shown at step G of FIG. 2. The variable portion of the linker of FIG. 6 is GGCGAA (as shown in the marked box).

The clone of FIG. 7 comprises a portion of a linker GN5 (marked in the box of FIG. 7) corresponding to nucleotide 12 to nucleotide 49 of SEQ ID NO: 1. The nucleotides 1 to 11 (included) of SEQ ID NO:1 were cleaved as shown at step G) of FIG. 2. The variable portion of the linker of FIG. 7 is GGCGAA (as shown in the marked box).

Then, the long G-stretches of the G-tailing methodology may interact with surrounding sequences and form very strong secondary structures, and this phenomenon affects the efficiency of sequencing, transcription and translation. On the contrary, the linker according to the present invention does not have these drawbacks.

Further, terminal deoxynucleotidyl transferase used for the G-tailing reaction requires the presence of heavy metals, like $MnCl_2$ or $CoCl_2$. These heavy metals cause degradation of cDNAs and decreased long strand full-coding/full-length cDNA content. Also this problem is solved using the linker according to the present invention, which does not require heavy metals and can be performed at low temperature, for instance, 4-37° C., preferably 12-20° C., or preferably 15° C.

According to another embodiment of the present invention, the constant portion of the linker of the present invention can comprise a marker. For example, a specific oligonucleotide sequence, a specific sequence or combination of sequences, that is easily recognizable.

The presence of this marker is very useful in order to distinguish and not to confuse libraries of different tissues (for instance, liver, brain, lungs, and the like) for the same or for different species, or libraries of different species (for instance, human, mouse, Drosophila melanogaster, rice, and the like).

In fact, when many kinds of libraries obtained from different tissues and/or species are constructed in the same laboratory and used for large-scale sequencing, there is the risk of confusing or contaminating the libraries or clones at any stage of colony picking, DNA preparation, sequencing determination, clone banking, re-arraying, etc.

Individual marking of cDNAs allows the preparation of different marked cDNAs from several tissues, allowing tissue expression profiling by sequencing 3' ends (complementary to the 5' mRNA end) of mixed cDNA libraries.

EXAMPLES

The method and embodiments according to the present invention will now be illustrated with reference to the following examples.

Example 1

Linker Evaluation Using a Test cDNA

Linkers Preparation

The population of linker oligonucleotides were purchased from Gibco-BRL Life technologies. The oligonucleotides were distinguished in one single strand (single upper strand) (indicated as A and C, comprising the variable portion) and the other single strand (single lower strand) (indicated as B). Then, one of A and C and B were bound together in order to form two different populations of double strands. The population of linkers A comprises linkers having a fixed portion oligonucleotide (in this case, bases 1-43 of SEQ ID NO:1) and a variable portion ($GN_5$), wherein the first base is G (that is, the base number 44) and the following bases NNNNN (bases from 45 to 49) different for each linker of the population and prepared at random.

The population of linkers C comprises a constant portion oligonucleotide (bases 1-43 of SEQ ID NO:3) and the variable portion NNNNNN (bases 44 to 49) different for each linker of the population and prepared at random.

A) $GN_5$ A strand, (SEQ ID NO: 1)
5'-AGAGAGAGAGCTCGAGCTCTATTTAGGTGACACTATAGAACCAGNN

NNN-3';

B) B strand, (SEQ ID NO: 2)
5'-TGGTTCTATAGTGTCACCTAAATAGAGCTCGAGCTCTCTCTCT-3';

The B strand was also phosphorylated at the 5' end when it was synthesized.

C) $N_6$ C strand, (SEQ ID NO: 3)
5'-AGAGAGAGAGCTCGAGCTCTATTTAGGTGACACTATAGAACCANNN

NNN-3'.

For degenerate nucleotides, V stands for A, G or C and N stands for any nucleotide, according to the international convention and to the Patentin Standard 2.1 Manual.

These oligonucleotides were purified by denaturing polyacrylamide gel electrophoresis (Sambrook, J., Fritsch, E. F., and Maniatis, T. (1989) "Molecular Cloning: A Laboratory Manual," Cold Spring Harbor Laboratory Press, Cold Spring Harbor, N.Y.) in order to remove contaminants that may have non-specific sites or lack annealing sites. Two populations of linkers named $GN_5$ and $N_6$ were prepared. The linker $GN_5$ was made by oligonucleotides AB (SEQ ID NO: USEQ ID NO:2) and the linker $N_6$ was made by oligonucleotides CB (SEQ ID NO:3/SEQ ID NO:2). They were prepared by mixing the oligonucleotides with NaCl (final concentration, 100 mM) and incubating at 65° C. for 5 min, 45° C. for 5 min, 37° C. for 10 min and 25° C. for 10 min.

The linkers prepared were then used for annealing to and ligating with single stranded DNA(s).

Test cDNA

To establish the appropriate linker when preparing cDNA libraries, a test first strand cDNA was generated from 5 µg 7.5-kb poly(A)-tailed RNA (Life Technologies) according to the method described in Carninci and Hayashizaki, 1999, except that CAP-Trapping was omitted. [$\alpha$-$^{32}$P]dGTP was incorporated at the reverse-transcription step. The amount of the produced first strand cDNA was estimated according to the incorporation ratio of radioactivity. Then, 50 ng of the 7.5-kb cDNA and various amounts (200 ng to 2 µg) (see also description of FIG. 3) of linker ($N_6$ or $GN_5$), prepared in the above step of Example 1, were combined together and ligated in a 30 µL reaction volume. The reactions were incubated overnight at 10° C.

After ligation, to remove excess linkers, linker-bound single stranded cDNA samples were incubated with 0.2 mg/mL proteinase K in 10 mM EDTA/0.2% SDS (reaction volume, 40 µL) at 45° C. for 15 min. The reaction products were extracted by using phenol/chloroform 40 µL. Then, the phenol/chloroform mixture was treated with 60 µL column buffer (10 mM Tris-HCl, 1 mM EDTA, 0.1 M NaCl, 0.1% SDS; pH 7.5) in order to extract the reaction product which was still remaining in the interface of the phenol/chloroform mixture. The reaction products extracted were loaded on a Sephacryl™-300 gel-filtration column (Amersham Pharmacia Biotech) and purified by centrifugation at 400×g for 2 min. The eluted fractions (comprising the purified linker-first strand cDNA samples) were precipitated by using isopropanol.

The control sample (comprising the single stranded Test cDNA but no linker) was used for the synthesis of the second strand cDNA. To assess the ability of the present method to support the synthesis of second-strand cDNA, 10 ng of the purified linker-ligated samples (Lanes 1-6 of FIG. 3) and unligated 7.5-kb first-strand cDNA as a control (Lane 7 of FIG. 3) were independently combined in a 10-µL reaction solution containing 1 µL 10× ExTaq™ buffer, 1 µL 2.5 mM dNTPs, 0.5 µL [$\alpha$-$^{32}$P]dGTP, and 0.5 µL Ex-Tag™ (Takara). The obtained samples were incubated at 65° C. for 5 min, 68° C. for 30 min, and 72° C. for 10 min and then analyzed by using alkaline gel electrophoresis.

The alkaline gel electrophoresis was performed by adding 5 µl of the samples to 1 µl of 6× Alkaline dye (Sambrook, Molecular Cloning, 6.7, 6.12). The electrophoresis gel used contained 0.8% of agarose, 50 mM NaOH and 5 mM EDTA and the buffer contained 50 mM NaOH and 5 mM EDTA (Sambrook, Molecular Cloning).

Results

Lanes 1-3 show the ligation of 50 ng between single stranded Test cDNA and respectively 200 ng, 500 ng and 2 g of linker $GN_5$.

Lanes 4-6 show the ligation between 50 ng of single stranded Test cDNA and respectively 200 ng, 500 ng and 2 µg of linker $N_6$.

Lane 7 is the control. 10 ng of first strand cDNA were added to 10-µL reaction solution comprising 1 µL 10× ExTaq™ buffer, 1 µL 2.5 mM dNTPs, 0.5 µL [α-$^{32}$P]dGTP, and 0.5 µL Ex-Taq™ (Takara). The sample was incubated at 65° C. for 5 min, 68° C. for 30 min, and 72° C. for 10 min. The single stranded cDNA was extended by forming a hairpin structure to form a second strand cDNA. This was detected at 15 kb in the alkaline gel electrophoresis.

Lane 8 is a sample of the first strand cDNA (23 ng) (without linker). This is detected at 7.5 kb.

Lane 9 represents the markers.

The electrophoresis of FIG. 3 shows that in Lanes 1-6, the ligation was particularly efficient (spots at level of 7.5 kb) and the amount of no ligation was negligible (spots at level of 15 kb).

Example 2

Full-Length cDNA Library Preparation and cDNA Analysis

Linker Preparation

Linkers were prepared as above described in Example 1.

Preparation of RNA

Slices of mouse liver tissue (0.5-1 g) were homogenized in 10 ml of a suspension and extracted with 1 ml of 2M sodium acetate (pH 4.0) and the same amount of a mixture of phenol/chloroform (volume ratio 5:1). After the extraction, the same volume of isopropanol was added to the aqueous layer to precipitate RNA. This sample was incubated on ice for an hour and centrifuged at 4000 rpm for 15 minutes with cooling to collect the precipitates. The resulting precipitates were washed with 70% ethanol and dissolved in 8 ml of water. By adding 2 ml of 5M NaCl and 16 ml of an aqueous solution (pH 7.0) containing 1% CTAB (cetyltrimethylammonium bromide), 4M urea and 50 mM Tris, RNA was precipitated and polysaccharides were removed (CTAS precipitate). After centrifugation at 4000 rpm for 15 minutes at room temperature, the RNA was dissolved in 4 ml of 7M guanidine-Cl. Then, two-fold amount of ethanol was added to the solution, incubated for an hour on ice and centrifuged at 4000 rpm for 15 minutes. The resulting precipitates were washed with 70% ethanol and collected. The precipitates were again dissolved in water and purity of RNA was determined by measuring OD ratio 260/280 (>1.8) and 230/260 (<0.45). The total RNA thus obtained was then purified by using the mRNA isolation kit for total RNA MACS™ (Miltenyi Biotech, Germany) and those samples containing poly A+ were concentrated.

cDNA Synthesis 5 to 10 µg of this polyA+ rich RNA, 5 µg of the first-strand primer containing a BamHI site 5'-(GA)$_5$AGGATCCAA-GAGCTC(T)$_{16}$VN-3') (SEQ ID NO:4) and 11.2 µl 80% glycerol were combined in a total volume of 24 µl. The RNA/primer mixture was denatured at 65° C. for 10 min. In parallel, in a final volume of 76 µl, 18.2 µl 5× first-strand synthesis buffer, 9.1 µl 0.1 M DTT, 6.0 µl 10 mM (each) dTTP, dGTP, dATP, and 5-methyl-dCTP (instead of dCTP), 29.6 µl saturated trehalose (approximately 80%, low metal content; Fluka Biochemika), and 10.0 µl Superscript H reverse transcriptase (200 U/µl) were combined, 1.0 µl [α-$^{32}$P]dGTP was placed in a third tube. The mRNA, glycerol, and primers were mixed on ice with the solution containing the Superscript, and an aliquot (20%) was quickly added to the tube containing the [α-$^{32}$P]dGTP. First-strand cDNA syntheses were performed in a thermocycler with a heated lid (e.g., MJ Research) according to the following program: step 1, 45° C. for 2 min; step 2, gradient annealing: cool to 35° C. over 1 min; step 3, complete annealing: 35° C. for 2 min; step 4, 50° C. for 5 min; step 5, increase to 60° C. at 0.1° C. per second; step 6, 55° C. for 2 min; step 7, 60° C. for 2 min; step 8, return to step 6 for 10 additional cycles. Incorporation of radioactivity allowed the estimation of the yield of cDNA (Carninci and Hayashizaki, 1999). The cDNA was treated with proteinase K, phenol/chloroform and chloroform-extracted, and ethanol-precipitated by using ammonium acetate as the salt (Carninci and Hayashizaki, 1999).

mRNA Biotinylation

Before biotinylation, the diol group of the cap and 3' end of mRNA was oxidized in a reaction solution in a final volume of 50 µl, containing the resuspended mRNA/cDNA comprising first-strand cDNA, 66 mM sodium acetate (pH 4.5), and 5 mM NaIO$_4$. Samples were incubated on ice in the dark for 45 min. mRNA/cDNA hybrids were then precipitated by adding 0.5 µl of 10% SDS, 11 µl NaCl, and 61 µl of isopropanol. After incubation in the dark on ice for 45 min, the sample was centrifuged for 10 min at 15,000 rpm. Finally the mRNA/cDNA hybrids were rinsed twice with 70% ethanol and resuspended in 50 µl of water. Subsequently, the cap was biotinylated in a final volume reaction solution of 210 µl by adding 5 µl M sodium acetate (pH 6.1), 5 µl 10% SDS, and 150 µl of 10 mM biotin hydrazide long-arm (Vector Biosystem). After overnight (13 hours) incubation at room temperature, the mRNA/cDNA hybrids were precipitated by adding 75 µl 1 M sodium acetate (pH 6.1), 5 µl 5 M NaCl, and 750 µl absolute ethanol and incubated on ice for 1 hour. The mRNA/cDNA hybrids were pelleted by centrifugation at 15,000 rpm for 10 min; then the pellet was washed once with 70% ethanol and once with 80% ethanol. The mRNA/cDNA hybrids were then resuspended in 70 µl 0.1×TE (1 mM Tris [pH 7.5], 0.1 mM EDTA).

Adsorption and Release of Full-Length cDNA

500 µl of MPG-streptavidin beads and 100 µg DNA-free tRNA were combined and the obtained mixture incubated on ice for 30 min with occasional mixing. The beads were separated by using a magnetic stand for 3 minutes, and the supernatant was removed. The beads were then washed three times with 500 µL washing/binding solution (2 M NaCl, 50 mM EDTA [pH 8.0]).

At the same time, 1 unit of RNase I (Promega) per 1 µg of starting material mRNA was added to the mRNA/cDNA hybrid sample in the buffer provided with the enzyme product (final volume, 200 µl); the sample was incubated at 37° C. for 15 min. To stop the reaction, the sample was put on ice and 100 µg tRNA and 100 µl of 5 M NaCl were added. To adsorb the full-coding/full-length in RNA/cDNA hybrids, the biotinylated, RNase I-treated mRNA/cDNA and the washed beads, which were resuspended in 40 µl of the washing/binding solution, were combined. After mixing, the tube was gently rotated for 30 min at room temperature. Full-coding/full-length cDNA was adsorbed on the beads, and the shortened cDNAs did not. The beads were separated from the supernatant with a magnetic stand. The beads were gently washed to remove the nonspecifically adsorbed cDNAs. Two washes with washing/binding solution were performed: one with 0.4% SDS, 50 µg/ml tRNA; one with 10 mM Tris-HCl (pH 7.5), 0.2 mM EDTA, 40 µg/ml tRNA, 10 mM NaCl, and 20% glycerol; as well as with 50 µg/ml tRNA in water.

The cDNA was released from the beads by adding 50 µl 50 mM NaOH, 5 mM EDTA and incubating for 10 min at room temperature with occasional mixing. The beads then were removed magnetically, and the eluted cDNA was transferred on ice to a tube containing 50 µl 1 M Tris-HCl, pH 7.0. The elution cycle was repeated once or twice with 50 µl-aliquots of 50 mM NaOH, 5 mM EDTA until most of the cDNA (80 to 90%, as measured by monitoring the radioactivity with a hand-held monitor) were recovered from the beads.

To remove traces of RNA, 1 µl RNase 1 (10 U/µl) was quickly added to the recovered cDNA on ice; the sample was then incubated at 37° C. for 10 min. The cDNA was treated with proteinase K, and then phenol/chloroform-extracted, and back-extracted. Then, the samples were concentrated by using one round of ultrafiltration with a Microcon 100 (Millipore) for 40-60 min at 2000 rpm.

CL-4B Spin-Column Fractionation of cDNA

The cDNA samples were then treated with CL-4B chromatography (Carninci and Hayashizaki, 1999) according the manual (S-400 spin column, for example of Amersham-Pharmacia, can also be used).

cDNAs-Linker Ligation

Cap-Trapper full-length single strand cDNAs, prepared as above, were divided in three different tubes. One for G-tailing, the second one for $GN_5$ linker ligation and the last one for $N_6/GN_5$ mixed linker ligation. An aliquot of 200 ng of cDNA were tailed with dG homopolymer as described in the prior art and used for the control cDNA library preparation (Carninci et al., Genomics, 1996).

300 ng of Cap-Trapper full-length first strand cDNAs were used as substrate for the linker-ligation using the linkers prepared as above by Gibco-BRULife Technologies, and cDNA libraries were constructed (shown in FIGS. 1 and 2).

300 ng of the single strand cDNA were added to 800 ng of a mixture of $N_6/GN_5$ linkers at proportion 1:4, and to 800 ng of $GN_5$ linker.

Ligation substrates (the cDNA/linker prepared as above), Solution I and Solution II (Ligation Kit, Takara) were mixed in ratio 1:2:1 and all the processes were performed as described in the manual provided with the product. The reaction volume therefore was of 30 µl and contained 7.5 µl of sample, 15 µl of Solution 1 and 7.5 µl of Solution II. The reaction run overnight at 10° C. (FIG. 2E).

Isolation from Excess Linkers.

After annealing and ligation between cDNA and linker, gel filtration was carried out. 30 µl of linker-ligation samples, as above, were treated with 0.2 mg/ml proteinase K in the presence of 10 mM EDTA and 0.2% SDS. They were incubated at 45° C. for 15 min, followed by the phenol/chloroform extraction. The samples were back extracted with 60 µl of column buffer (10 mM Tris-HCl, 1 mM EDTA, 0.1 M NaCl, 0.1% SDS, pH 7.5), Subsequently, the samples were subjected to spun column gel filtration over Sephacryl S 300 (Amersham Pharmacia Biotech). In the step for the spun column, the centrifugation was carried out at 400×g for 2 min. The eluted fraction was recovered and precipitated with isopropanol.

After the purification step, the second strand cDNA synthesis was carried out (FIG. 2F).

To synthesize the second-strand cDNA, all purified linker-ligated samples were used. 6 µl of 10× ExTaq™ buffer Takara, and 6 µl of 10 mM dNTPs and 0.5 µl [$\alpha$-$^{32}$P]dGTP were added to the tubes in 60 µl. The samples were pre-incubated at 72° C. for 15 sec and then 0.5 µl of ExTaq™ were added. Then they were incubated at 72° C. for 30 min.

The samples were analyzed by alkali gel electrophoresis, that is, 0.5 µl of the samples comprising the synthesized second-strand were added to 1 µl of 6× Alkaline dye (Sambrook, Molecular Cloning, 6.7, 6.12) in final volume of 6 µl and the electrophoresis was performed.

The electrophoresis is performed using an agarose gel containing 0.8% of agarose, 50 mM NaOH, 5 mM EDTA and electrophoresis buffer containing 50 mM NAOH and 5 mM EDTA (Sambrook, Molecular Cloning).

The samples were purified with phenol/chloroform followed by ethanol precipitation under standard condition (Sambrook, J., Fritsch, E. F., and Maniatis, T. (1989) "Molecular Cloning: A Laboratory Mammal," Cold Spring Harbor Laboratory Press, Cold Spring Harbor, N.Y.).

Subsequently, cDNA was cleaved with Bam HI (25 U/µg of cDNAs) and Xho I (25 U/µg of cDNAs) at 37° C. for 1 h and extracted with phenol/chloroform. The aqueous phase was purified with a CL4B gel filtration spin column (Amersham Pharmacia Biotech) followed by ethanol precipitation as described in presence of 2 µg of glycogen (Carninci and Hayashizaki, 1999).

Construction of pBS IV Vector 10 ng pBS SK+ (Stratagene), 20 µl 10×NEB buffer 2 (New England Biolabs, Inc), 20 µl 10 mg/ml bovine serum albumin (NEB), 30 units Not I (NEB), 30 units Kpn I (NEB) and 10 units Xho I (NEB) were mixed in the volume of 200 µl and incubated at 37° C. for 2 hours. Then, this mixture was subjected to electrophoresis at 50V for 1 hour on 0.8% SeaPlaque agarose gel (FMC Bioproducts)/1×TAE buffer/0.5 µg/ml ethidium bromide (8 cm×8 cm) in 1×TAE/0.5 µg/ml ethidium bromide buffer to separate a long plasmid part from a short DNA section (Molecular Cloning). The long plasmid part was cut out from the gel and the gel was transferred to a tube. Cleaved plasmid was extracted and purified by the GENECLEAN II™ Kit (Bio 101 Inc.). Concentration and purity of the plasmid were checked by agarose gel electrophoresis, comparing with a standard plasmid, which concentration was already known.

Double Strand Oligonucleotide Preparation

The oligonucleotides used were custom-synthesized (Life Technologies-Life Tech Oriental, Tokyo, Japan) and then purified by using denaturing polyacrylamide gel electrophoresis in order to remove contaminants (Maniatis etc.). The Not/Kpn double stranded oligonucleotide was prepared by mixing the following two single stranded oligonucleotides:

one strand (Upper-strand) (5'GGCCGCATAACTTCG-TATAGCATACATTATACGAAGTTATG-GATCAGGCCAAA TCGGCCGAGCTCGAATTCGTC-GACGAGAGACTGCAGGAGAGAGGATCCGGTA C-3') (SEQ ID NO:6); and the other strand (Lower-strand) (5'CGGATCCTCTCTCCT-GCAGTCTCTCGTCGACGAATTC-GAGCTCGGCCGATTT GGCCTGATCCATAACTTCG-TATAATGTATGCTATACGAAGTTATGC-3') (SEQ ID NO:7) in NaCl (final concentration, 100 mM).

This mixture was then incubated at 65° C. for 5 min, 45° C. for 5 min, 37° C. for 10 min, and 25° C. for 10 min, Vector-Oligonucleotide Ligation 100 ng of this plasmid, which has Kpn I and Not I sites at the end, were mixed with 3 ng of a Not/Kpn double stranded oligonucleotide, 1 µl 10× ligation buffer (NEB) and T4 DNA ligase (NEB) in 10 µl.

Cell Transformation

A tube comprising the ligation sample was then incubated overnight at 16° C. The ligation sample was mixed with 250 mM NaCl, 1 µg glycogen and isopropanol, then precipitated to remove buffer. Then, it was dissolved with 10 µl sterile water. 1 µl of the obtained sample was supplied to transform to a suspension of E. coli cells DH10B (Life tech oriental) by electroporation (following the Protocol of the Manufacturer). The transformed cell was selected on LB plate containing 100 µg/ml ampicillin. The ampicillin-resistant clone was cultured in the LB liquid medium containing 100 µg/ml ampicillin at 37° C. for 16 h with shaking. The recombinant plasmid used for the insertion of the synthesized double strand oligonucleotide was purified by the alkali-SDS method (Molecular Cloning). The inserted sequence was confirmed with the M13 forward primer (SEQ ID NO:5) and the Big dye kit by ABI377 DNA sequencer (PE-Applied BioSystems).

Vector Preparation

10 μg of the modified pBS SK (+) plasmid obtained as above (named pBS IV) were mixed with 20 μl 10×Bam HI buffer, 20 μl 10 mg/ml bovine serum albumin (New England Biolabs, Inc), 30 units BamH I (New England Biolabs, Inc), 30 units Sal I (New England Biolabs, Inc), adjusted to a volume of 200 μl and incubated at 37° C. for 1.5 hours. Then, 10 units Pst I (New England Biolabs, Inc) were added to the mixture in a tube and incubated for 30 min. Furthermore, dephosphorylation of the plasmid end was carried out by 0.5 units thermo-sensitive alkaline phosphatase TsAP (Life Technologies), TsAP makes the background resulting from partially cut plasmid low, since dephosphorylated ends cannot ligate to each other. The tube was incubated at 37° C. for 30 min. To inactivate TsAP, EDTA (final concentration of 20 mM) was added and the sample incubated at 65° C. for 30 min. The restriction enzyme/TsAP treated plasmid was separated as described above in the vector construction step. The band corresponding to linear plasmid, which has Bam HI and Sal I site at the end, was cut out from the gel and sliced to small pieces. It was put in a tube containing 500 μl 1×β agarase buffer (NEB) and left on ice for 30 min. The buffer was changed once and the sample was left on ice 30 more min.

This sample was incubated at 65° C. for 10 min to melt the gel. β-agarase buffer was added to bring the solution to 100 μl. Then, it was cooled at 45° C. for 3 min and β-agarose (NEB) was added to the concentration of 3 U/100 μl reaction. This reaction solution was incubated at 45° C. for 6 h. 10 μl of 5M NaCl and 100 μl of phenol/chloroform were added to the tube. The tube was inverted gently for 5 min and centrifuged at 15 krpm for 3 min at room temperature. The aqueous phase was recovered and followed by chloroform extraction and isopropanol precipitation. The tube was centrifuged at 15 krpm for 10 min at 4° C. and the obtained pellet was washed with 80% ethanol twice. Finally, the pellet was dissolved with sterile water to a final concentration of 100 ng/μl. The vector concentration and purity were checked by agarose gel electrophoresis, comparing with standard plasmid, which concentration was already known.

Cloning 10 ng of cDNA, obtained in the previous step, were ligated overnight to 190 ng of the aforementioned modified vector pBluescript KS (+)(Stratagene).

The cDNA-vector ligations were precipitated with 2.5 times volume of EtOH. The samples were introduced into *E. coli* DH10B (Gibco BRL) by electroporation. The transformed cells were applied on an LB plate containing 100 μg/ml ampicillin and cultured overnight at 37° C. 36 colonies were picked up randomly and cultured in LB ampicillin (100 μg/ml) liquid medium overnight at 37° C. Recombinant plasmids were extracted from 3 cultures (Sambrook et al., 1989). These 3 purified plasmids were sequenced from the 5' end with the M13 forward primer TGTAAAACGACGGCCAGT (SEQ ID NO:5) with the Big Dye Terminator Cycle Sequencing Ready Reaction Kit (PE-ABI) by using the ABI3700 DNA sequencer (PE-Applied BioSystems) according to the Kit Manual Instruction.

Example 3

Efficiency of Ligation

In the ligation of linkers prepared as above to the mouse liver derived cDNAs, 2 μg of mixed linker ($N_6$:$GN_5$=1:4) were ligated to various amounts of cDNAs (1 μg, 0.5 μg and 0.2 μg respectively in Lanes 1, 2 and 3 of FIG. 4). Then, 50 ng of ligated cDNAs were used for the second strand synthesis and analyzed by alkaline gel electrophoresis. All electrophoresis patterns and incorporation rates were the same (Lanes 1-3), suggesting that 2 μg of linker were efficiently ligated to any of the different amount of cDNAs. If the linker amount was not appropriate, excessively expressed cDNA bands would be shifted up to twice size by forming hairpin structures. Instead, the first-strand cDNA and all second-strand cDNAs showed the same pattern (the same size).

Example 4

Efficiency of Linker-Ligation Full-Length cDNAs Preparation

Liver mouse cDNA libraries were prepared in the same way as above described using the CAP-trapper technology.

Whether those prepared by the linker method as described in the above example are full-length cDNA was checked by confirming the presence of an ATG starting codon after a sequencing step. In fact, those cDNAs containing the full-coding sequence from the starting ATO were accepted as full-length cDNAs. The 5' sequences were compared with the public nucleotide database using BLAST (Altschul, S. F., Gish, W., Miller, W., Myers, E. W. & Lipman, D. J., 1990, "Basic local alignment search tool." J. Mol. Biol. 215:403-410).

Nucleotide Sequences were determined using Big Dye Terminator Cycle Sequencing Ready Reaction Kit (PE-ABI) and the Perkin Elmer-Applied Biosystems ABI 3700 according to the Kit Manual Instructions.

The sequencing primer used is the M13 primer on the 5' side (SEQ ID NO:5).

The data are reported in Table 1. The presence of ATG (from which the transcription starts) has been marked with the corresponding position. For example, with reference to sample 2.01, the adenosine of the ATG codon has the position 63; this indicates that this cDNA sequence has a 62 by 5'-UTR.

TABLE 1

| Sample code | Gene | Public db ID | RIKEN db ID | Existence and position of ATG |
|---|---|---|---|---|
| 1) N6/GN5 mixed linker (1:4) | | | | |
| 2.01 | *M. musculus* alpha fetoprotein | gi\|6680667\| | ZX00047P08 | 63 |
| 2.05 | Human cDNA FLJ10604 fis | gi\|7022741\| | ZX00036I09 | 172 |
| 2.22 | Mouse mMCM2 | gi\|2381484\| | — | 37 |
| 2.25 | *M. musculus* epsilon 14-3-3 isoform | gi\|57965\| | — | 104 |
| 2.26 | *M. musculus* SH2-containing inositol phosphatase SHIP | gi\|1255351\| | — | 105 |
| 2.28 | *M. musculus* calmodulin 3 | gi\|6680833\| | R000011E16 | 176 |
| 2.30 | *M. musculus* EAT/MCL-1 | gi\|2522268\| | — | 61 |
| 2.31 | *M. musculus* heterogenous nuclear ribonucleoprotein U | gi\|3329495\| | — | 199 |
| 2.33 | *H. sapiens* hDj9 | gi\|6567165\| | ZX00052D18 | 166 |
| 2.36 | *M. musculus* Lsc (lsc) oncogene | gi\|1389755\| | ZX00048L03 | 214 |

TABLE 1-continued

| Sample code | Gene | Public db ID | RIKEN db ID | Existence and position of ATG |
|---|---|---|---|---|
| | 2) GN5 linker | | | |
| 3.07 | *M. musculus* ornithine decarboxylase antizyme | gi|1279827| | ZX00047L07 | 81 |
| 3.09 | *R. norvegicus* guanosine monophosphate reductase | gi|3907578| | R000001H02 | 131 |
| 3.10 | Mouse calmodulin | gi|469421| | R000011E16 | 192 |
| 3.13 | *M. musculus* protein phosphatase 5 | gi|2407636| | — | 89 |
| 3.16 | *Rattus* sp. calcium-regulated heat stable protein CRHSP-24 | gi|4583308| | R000016L20 | 59 |
| 3.20 | Murine mRNA with homology to yeast L29 ribosomal protein | gi|50320| | ZX00047I16 | 30 |
| 3.21 | *M. musculus* ribosomal protein S3 | gi|439521| | ZX00048P23 | 39 |
| 3.23 | *M. musculus* melanome X-actin | gi|6671508| | ZX00035N19 | 88 |
| 3.29 | *H. sapiens* CGI-47 protein | gi|4929562| | ZX00048M14 | 199 |
| 3.33 | *M. musculus* mini chromosome maintenance deficient 6 | gi|6678831| | — | 131 |
| 3.34 | *M. musculus* membrane protein TMS-1 | gi|5853318| | R000009P22 | 60 |

These data show that cDNAs are efficiently prepared and sequenced using the linker methodology according to the present invention.

The sequencing of clone 2.05 of Table 1 is shown in FIG. 6.

The sequencing of clone 3.07 of Table 1 is shown in FIG. 7.

Advantages of the CAP-Trapping-Linker Versus the Conventional G-Tailing CAP-Trapping I) Control of G-tail length has been difficult over the years. To anneal the second strand primer, cDNA clones have at least 11 of dGs with an average of 13-15 dGs. Although the G-tailing reaction is self-limiting to 15-30 nt (Hyone-Myong Eun, 1996, Enzymology Primer for Recombinant DNA Technology, page 477), G-stretches longer than about 20 bases, which were often obtained, caused a dramatic decrease of sequencing yield or in the worst case failure, while shorter G stretches impaired long sequence reading (see FIG. 5). During sequencing, long G-stretches may interact with surrounding sequences and form very strong secondary structures. This may be problematic in case of interactions with 5' UTRs that are typically GC rich. This is especially serious in full-length cDNAs synthesis like in the case of Cap-Trapping libraries.

The method using the linker according the present invention, different from conventional methods, does not have such a drawback (even if the random variable portion comprises G, there are statistically a small number of G residues) and can allow efficient sequencing (FIGS. 6 and 7).

II) A G-stretch is expected to affect the efficiency of translation in case of functional studies, for instance where protein expression is required, such as in expression cloning (King R W, Lustig K D, Stukenberg P T, McGarry T J, Kirschner M W. "Expression cloning in the test tube", Science 1997; 277:973-4). On the other hand, the linker sequence of the present invention does not inhibit transcription and translation.

Industrial Applicability

The present invention provides a novel and efficient method for the preparation of cDNA libraries. More specifically, the present invention provides a novel linker that can be used instead of G-tailing in a method for the preparation of cDNA libraries and to provide a method for the preparation of cDNA libraries using said linker.

What is claimed is:

1. A method of preparing a double strand polynucleotide comprising:
   i) mixing a population of linkers and a population of a single strand polynucleotides that are first strand cDNA to obtain a mixture comprising a population of linkers and a population of single strand polynucleotides, wherein the linkers comprise a first oligonucleotide strand comprising a fixed portion and a variable portion, and a second oligonucleotide strand comprising a fixed portion complementary to the fixed portion of the first oligonucleotide strand, and said first and second oligonucleotide strands are annealed together to form a double-stranded fixed portion so that the variable portion of said first oligonucleotide strand is overhanging, and
   wherein said double-stranded fixed portion of the linkers has a common sequence among all of the linkers of the population and comprises at least one restriction enzyme site, recombination site, RNA polymerase promoter site, marker or tag sequence, and the overhanging variable portion of said linkers is represented by the formula (G)m(N)n-m wherein N is A, C, G, T or U, n is an integer from 5 to 10, m is an integer from 1 to 3, the nucleotides (N) may be the same or different from each other, and nucleotides (G)m in the formula (G)m(N)n-m are located adjacent to the double-stranded fixed portion of the linkers, and wherein said population of linkers comprises linkers which have at least two different (N)n-m sequences,
   ii) annealing a variable portion of a first oligonucleotide strand of a linker to a target single strand polynucleotide that is contained in the population of single strand polynucleotides and that has a sequence complementary to said variable portion,
   iii) ligating the target single strand polynucleotide to a second strand of the linker, and
   iv) synthesizing a second single strand polynucleotide(s) complementary to said target single strand polynucleotide(s) by extending the first oligonucleotide strand of the linker to obtain the double strand polynucleotide.

2. The method according to claim 1, wherein said single strand oligonucleotide variable portion is represented as the formula (G)m(N)n-m is $GN_4$, $GN_5$, $G_2N_3$, or $G_2N_4$.

3. The method according to claim 1, wherein the first oligonucleotide strand of a linker comprises a single strand oligonucleotide having the sequence of SEQ ID NO:1.

4. The method according to claim 1, wherein the first oligonucleotide strand of a linker comprises the sequence of sequence SEQ ID NO:1 and the second oligonucleotide strand of the linker comprises a single strand oligonucleotide having the sequence of sequence SEQ ID NO:2.

5. A method of preparing a double strand polynucleotide comprising:

i) mixing at least a first population of linkers, a second population of linkers, and a population of a single strand polynucleotides that are first strand cDNA to obtain a mixture comprising a population of linkers and a population of single strand polynucleotides, wherein the first population of linkers comprises a first oligonucleotide strand comprising a fixed portion and a variable portion, and a second oligonucleotide strand comprising a fixed portion complementary to the fixed portion of the first oligonucleotide strand, and said first and second oligonucleotide strands are annealed together to form a double-stranded fixed portion so that the variable portion of said first oligonucleotide strand is overhanging, and wherein said double-stranded fixed portion of the linkers has a common sequence among all of the linkers of the population and comprises at least one restriction enzyme site, recombination site, RNA polymerase promoter site, marker or tag sequence, and the overhanging variable portion of said linkers is represented by the formula $(G)m(N)n-m$ wherein N is A, C, Cy T or U, n is an integer from 5 to 10, m is an integer from 1 to 3, the nucleotides (N) may be the same or different from each other, and nucleotides (G)m in the formula $(G)m(N)n-m$ are located adjacent to the double-stranded fixed portion of the linkers, and wherein said first population of linkers comprises linkers which have at least two different $(N)n-m$ sequences, and wherein the second population of linkers comprises a population of $(N)n$ linkers, wherein the linkers of the $(N)n$ linker population comprise a first oligonucleotide strand comprising a fixed portion and a variable portion, and a second oligonucleotide strand comprising a fixed portion complementary to the fixed portion of the first oligonucleotide strand, and said first and second oligonucleotide strands are annealed together to form a double-stranded fixed portion so that the variable portion of said first oligonucleotide strand is overhanging, and wherein said double-stranded fixed portion of the $(N)n$ linkers has a common sequence among all of the linkers of the $(N)n$ linker population and comprises at least one restriction enzyme site, recombination site, RNA polymerase promoter site, marker or tag sequence, and the overhanging variable portion of said $(N)n$ linkers is represented by the formula $(N)n$ wherein N is A, C, G, T or U, n is an integer from 5 to 10, the nucleotides (N) may be the same or different from each other, and said variable portion $(N)n$ is located on the 3' side of the double-stranded fixed portion, and wherein said second population of $(N)n$ linkers comprises linkers which have at least two different $(N)n$ sequences, ii) annealing a variable portion of a first oligonucleotide strand of a linker to a target single strand polynucleotide that is contained in the population of single strand polynucleotides and that has a sequence complementary to said variable portion, iii) ligating the target single strand polynucleotide to a second strand of the linker, and iv) synthesizing a second single strand polynucleotide(s) complementary to said target single strand polynucleotide(s) by extending the first oligonucleotide strand of the linker to obtain the double strand polynucleotide.

6. The method according to claim 5, wherein the $(G)m(N)n-m$ linker population is a population of linkers having any variable portion selected from the group consisting of $GN_4$, $GN_5$, $G_2N_3$, and $G_2N_4$, and the $(N)n$ linker population is a population of linkers having any variable portion selected from the group consisting of $N_5$ and $N_6$.

7. The method according to claim 5, wherein the $(G)m(N)n-m$ linker population is a population of linkers having the variable portion of $GN_5$ and the $(N)n$ linker population is a population of linkers having the variable portion of $N_6$, or the $(G)m(N)n-m$ linker population is a population of linkers having the variable portion of $G_2N_4$ and the $(N)n$ linker population is a population of linkers having the variable portion of $N_6$.

8. The method according to claim 7, wherein the mixing ratio of the $(N)n$ linker population having the variable portion of $N_6$ and the $(G)m(N)n-m$ linker population having the variable portion of $GN_5$ ranges from 1:3 to 1:5.

9. The method according to claim 7, wherein the ratio of the $(N)n$ linker population having the variable portion of $N_6$ and the $(G)m(N)n-m$ linker population having the variable portion of $GN_5$ is 1:4.

10. The method according to claim 1, wherein ligation is performed by a ligase.

11. The method according to claim 10, wherein the ligase is a DNA ligase or a RNA ligase.

12. The method according to claim 11, wherein the DNA ligase is T4 DNA ligase or *E.coli* DNA ligase.

13. The method according to claim 10, wherein ligation is performed in the presence of a ligase-stimulating agent.

14. The method according to claim 13, wherein the ligase-stimulating agent is PEG (polyethylene glycol).

15. The method according to claim 1, wherein the linker and the target first strand polynucleotide or the second strand polynucleotide complementary to the target polynucleotide is DNA.

16. The method according to claim 15, wherein the obtained double strand polynucleotide is a full-length cDNA.

17. The method according to claim 16, wherein the first strand cDNA is obtained by Cap trapping at the 5' end of mRNA.

18. The method according to claim 17, wherein the Cap-trapped cDNA is further normalized or subtracted before or after the ligation to the linker.

19. The method according to claim 1, which further comprises a step of increasing temperature before annealing the linker to the target first strand polynucleotide and/or after synthesizing polynucleotide second strand.

20. The method according to claim 19, wherein the temperature ranges from 25 to 100° C.

21. The method according to claim 20, wherein the temperature is 65° C.

22. The method according to claim 1, wherein at least one end of the fixed portion of the linker, opposite to the variable portion, is tagged with a protective group.

23. The method of claim 22, wherein the protective group is $NH_2$.

24. The method of claim 1, wherein the ends of the two strands of the linker fixed portion are bound together by a loop.

25. The method according to claim 1, which further comprises a step in which said linker-polynucleotide is cleaved at both ends at restriction enzyme sites and inserted into a vector.

26. The method according to claim 1, which further comprises a step in which said linker-polynucleotide is cleaved to produce blunt ends and inserted into a vector.

* * * * *